(12) United States Patent
Spieth

(10) Patent No.: US 10,885,422 B2
(45) Date of Patent: Jan. 5, 2021

(54) THRESHOLD-VALUE DETECTION DEVICE

(71) Applicant: Hahn-Schickard-Gesellschaft für angewandte Forschung e.V., Villingen-Schwenningen (DE)

(72) Inventor: Sven Spieth, Dauchingen (DE)

(73) Assignee: Hahn-Schickard-Gesellschaft fur angewandte Forschung e.V., Villingen-Schwenningen (DE)

( * ) Notice: Subject to any disclaimer, the term of this patent is extended or adjusted under 35 U.S.C. 154(b) by 83 days.

(21) Appl. No.: 16/381,955

(22) Filed: Apr. 11, 2019

(65) Prior Publication Data
US 2019/0236435 A1 Aug. 1, 2019

Related U.S. Application Data

(63) Continuation of application No. PCT/EP2017/074948, filed on Oct. 2, 2017.

(30) Foreign Application Priority Data

Oct. 14, 2016 (DE) .................. 10 2016 220 111

(51) Int. Cl.
*G06K 7/10* (2006.01)
*G06M 1/08* (2006.01)
(Continued)

(52) U.S. Cl.
CPC ............. *G06M 1/083* (2013.01); *A61L 2/28* (2013.01); *B81B 3/0067* (2013.01);
(Continued)

(58) Field of Classification Search
CPC ........ G06M 1/083; G06M 1/101; G06M 1/27; A61L 2/28; B81B 3/0067; B81B 2201/02; G06K 19/0723
(Continued)

(56) References Cited

U.S. PATENT DOCUMENTS 5,359,993 A 11/1994 Slater et al.
2002/0113281 A1* 8/2002 Cunningham ........ B81B 3/0051
257/415
(Continued)

FOREIGN PATENT DOCUMENTS

DE 2518214 A1 11/1976
DE 102005054546 A1 5/2007
(Continued)

OTHER PUBLICATIONS

H. Mehner, C. Weise, S. Schwebke, .S. Hampl, M. Hoffmann, „A passive microsystem for detecting multiple acceleration events beyond a threshold, Microelectronic Engineering 145 (2015), 104-111, 2015, 104-111.
(Continued)

*Primary Examiner* — Karl D Frech
(74) *Attorney, Agent, or Firm* — Michael A. Glenn; Perkins Coie LLP

(57) ABSTRACT

A device has a latching mechanism including a catch element having at least two catches, and a pawl configured to engage in a catch interstice between two catches. The catch element is movable in relation to the pawl in a freewheeling direction, and a movement of the catch element in relation to the pawl in a blocking direction may be blocked by means of the pawl. The device further includes a deflectable actuator configured to move the catch element and the pawl relative to each other on a catch-by-catch basis in the freewheeling direction by means of deflection. According to the invention, the device also includes an electric component configured to change its electric property as a function of the catch-wise movement of the catch element in relation to the pawl.

18 Claims, 11 Drawing Sheets

(51) Int. Cl.
  *G06M 1/27* (2006.01)
  *A61L 2/28* (2006.01)
  *B81B 3/00* (2006.01)
  *G06K 19/07* (2006.01)
  *G06M 1/06* (2006.01)
  *G06M 1/10* (2006.01)

(52) U.S. Cl.
  CPC ........... *G06K 19/0723* (2013.01); *G06M 1/06* (2013.01); *G06M 1/101* (2013.01); *G06M 1/27* (2013.01); *B81B 2201/02* (2013.01)

(58) Field of Classification Search
  USPC .......... 235/492.1, 60.49, 91 A, 142, 144 PN, 235/144 TP
  See application file for complete search history.

(56) References Cited

U.S. PATENT DOCUMENTS

| | | |
|---|---|---|
| 2011/0234376 A1 | 9/2011 | Deichmeyer et al. |
| 2013/0104654 A1 | 5/2013 | Classen et al. |
| 2015/0022053 A1 | 1/2015 | Minotti et al. |

FOREIGN PATENT DOCUMENTS

| | | |
|---|---|---|
| DE | 102008039376 A1 | 2/2010 |
| DE | 102008039377 A1 | 2/2010 |
| DE | 102012200740 A1 | 5/2013 |
| DE | 202014005485 U1 | 8/2014 |
| EP | 0021761 A1 | 1/1981 |
| EP | 0979658 A1 | 2/2000 |
| EP | 1844838 A2 | 10/2007 |
| WO | 2005081730 A2 | 9/2005 |
| WO | 2010020413 A1 | 2/2010 |

OTHER PUBLICATIONS

Sun, Xi-Qing, et al., X.-Q. Sun, S. Zhou, and W. N. Carr, "A surface micromachined latching accelerometer", International Conference on Solid State Sensors and Actuators 1997, 1189-1192, 1997, 1189-1192.

* cited by examiner

THRESHOLD-VALUE DETECTION DEVICE

CROSS-REFERENCES TO RELATED APPLICATIONS

This application is a continuation of copending International Application No. PCT/EP2017/074948, filed Oct. 2, 2017, which is incorporated herein by reference in its entirety, which claims priority from German Application No. 10 2016 220 111.5, filed Oct. 14, 2016, which is incorporated herein by reference in its entirety.

The invention relates to a device comprising the features of claim 1.

The inventive device may detect most varied threshold-value events. Such threshold-value events are defined in that a predefined threshold value is fallen below or exceeded. Said threshold values may be, e.g., threshold values of a pressure, of a temperature, of an acceleration, of a mechanical force, and the like.

BACKGROUND OF THE INVENTION

Sensing and identifying such overshoots and/or undershoots of threshold values within a considered time period may be important in various industrial processes. One of innumerable examples relates, e.g., to critical temperature stresses during product manufacturing, in the logistics chain, during product utilization or, generally, in temperature-related processes performed on a product.

Nowadays, overshoots of acceleration threshold values, e.g. in drop sensors in smart phones, or overshoots of pressure threshold values, e.g. in gas bottles, are of high interest in industry. In this context, it is often interesting to learn how often a predefined threshold value has been fallen below or exceeded.

For example, WO 2005/081730 A2 describes a device for counting the number of sterilization and/or utilization cycles performed. Said device is implemented in precision engineering, which clearly differs from the increased requirements placed upon the precision of components manufactured in microsystems technology. The known device comprises a gearwheel or a rack, which are actuated by a piston in each case. The device comprises plug-type connectors by means of which the device may be plugged into an external apparatus. In the area of said plugs, an end of the piston is additionally arranged. When said device is plugged into the external apparatus, the piston will abut the external apparatus and will be displaced by the plug-in movement. Thus, the piston actuates the gear or rack and advances it by one tooth. An optical display means in the form of a mechanical numerical scale is used here so as to indicate the number of utilization cycles to the user.

DE 10 2005 054 546 A1 describes a system for sensing a treatment process being performed on an object. The device disclosed herein comprises a single arresting hook and a thermally deformable bimetal strip which actuates a counting switch in a non-actuated state. As the temperature increases, the bimetal strip is deflected toward the arresting hook and will be caught by the arresting hook in the process. Here, the bimetal strip actuates a safety switch arranged on the arresting hook. During readout of the device by means of RFID, a resetting device is actuated which pivots the arresting hook back, so that the bimetal strip falls back onto the counting switch. However, this will only take place once the temperature has already decreased sufficiently so that the bimetal strip again urges back into its non-deflected position. However, the much larger problem in this device consists in the fact that the mechanism does not reset itself, i.e. a readout may be effected by means of RFID after each sterilization process for the resetting mechanism to be actuated. However, if one forgets to read out the device in between two applications in surgery, for example, it will not be possible to verify afterwards whether sterilization has actually taken place between the two surgeries or whether the bimetal strip is still clinging to the arresting hook because of the sterilization performed prior to the first surgery.

[1] describes a micromechanical threshold-value counter for enumerating up to five acceleration threshold-value events. A bending beam having a mass arranged thereon is cantilevered, and its open end is arranged within a comb-like element exhibiting gaps. Upon acceleration, the mass arranged on the bending beam is deflected as a function of the amount of acceleration, so that the open end of the bending beam comes to rest within one of the gaps of the comb-like element. Said device is a passive system requiring no additional drive elements. However, this device offers no resetting mechanism, i.e., once the bending beam is deflected, it will not automatically restore itself to the initial position. Apart from that, the mass reacts to the amount of acceleration only but not to the number of acceleration events, i.e. with one single but intense acceleration event, the open end of the bending beam may jump forward by two or more gaps. Therefore, one cannot ensure, with said device, that said jumping forward takes place only by one catch per threshold-value event. Thus, one cannot differentiate afterwards whether one very intense acceleration event has taken place or whether several mild acceleration events have taken place.

A similar system is described in [2]. A seismic mass is suspended at two springs. The seismic mass is arranged within a stationary ratchet element. The ratchet element comprises projections, and the seismic mass comprises hooks which may engage into the projections. Said device essentially exhibits the same advantages and disadvantages as the system described in [1]. This device is also a passive system requiring no additional drive elements. However, this device, too, offers no resetting mechanism, which means that once the seismic mass has been deflected, it will not automatically reset itself into the initial position. Apart from that, here, too, the seismic mass reacts to the amount of acceleration only but not to the number of acceleration events, i.e. with one single but intense acceleration event, the seismic mass may jump forward by two or more projections. Therefore, one also cannot ensure with said device that said jumping forward takes place only by one catch per threshold-value event. Thus, one cannot differentiate afterwards whether one very intense acceleration event has taken place or whether several mild acceleration events have taken place.

SUMMARY

According to an embodiment, a device may have: a latching mechanism arranged on a substrate and having a catch element having at least two catches, and a pawl configured to engage in a catch interstice between two catches, wherein the catch element is movable in relation to the pawl in a freewheeling direction and wherein a movement of the catch element in relation to the pawl in a blocking direction may be blocked by means of the pawl, a deflectable actuator configured to move the catch element and the pawl relative to each other on a catch-by-catch basis in the freewheeling direction by means of a deflection, and an electric component configured to change its electric property as a function of the catch-wise movement of the catch element in relation to the pawl, wherein the latching mechanism is configured as a MEMS microsystem.

To this end, the inventive device comprises, among others, a latching mechanism. The latching mechanism comprises a catch element comprising at least two catches. Moreover, the latching mechanism comprises a pawl configured to engage into a catch interstice between two catches. The catch interstice is the gap between two catches. The catch element is movable in relation to the pawl in a first direction. Therefore, this first direction is also referred to as a freewheeling direction. A movement of the catch element in relation to the pawl in a second direction, however, may be blocked by means of the pawl. Said second direction is therefore also referred to as the blocking direction. Thus, the catch element may move relative to the pawl in the freewheeling direction. A movement of the catch element in the blocking direction is therefore prevented by the pawl. The inventive device further comprises a deflectable actuation means configured to move the catch element and the pawl relative to each other in the freewheeling direction on a catch-by-catch basis by means of deflection. The actuation means actuates, e.g., the catch element or the pawl so as to enable a relative movement between the catch element and the pawl. According to the invention, this relative movement takes place on a catch-by-catch basis only, however. This means that the catch element and the pawl are moved forward by one catch only with each deflection of the actuation means. Or put differently, the catch element and the pawl are moved, with each deflection of the actuation means, in relation to each other such that the catch element moves forward, in relation to the pawl, only step-by-step by one catch for each actuation. The actuation means pushes the catch element forward by one catch in relation to the pawl each time the threshold value is exceeded. To this end, the actuation means can reset itself into its initial position after the predefined threshold value has been fallen below or exceed. Thus, occurrences of threshold-value events may be detected multiple times. The actuation means here is the component which reacts sensitively to the quantity to be measured. This means that the actuation means may be deflected, e.g. in response to a force, a temperature, a pressure, an electrical current, and the like, such that it will actuate the catch element or the pawl and will move them in relation to each other by one catch, respectively, when a predefined threshold value of the quantity to be measured is fallen below or exceeded. In addition, the inventive device comprises an electric component configured to change its electric property as a function of the catch-wise movement of the catch element in relation to the pawl. For example, the electric component may change its electric property, e.g., each time the catch element has moved forward by one catch in relation to the pawl. In this context, the variable electric property of the electric component may adopt a specific value at each individual position of the catch element in relation to the pawl. For example, the electric component may be a variable resistor, a capacitor or a coil, the respective amount (resistance, capacitance, inductance) of which changes with each catch-wise movement of the catch element in relation to the pawl. Conversely, therefore, each individual resistance, capacitance or inductance value is characteristic of a specific position, respectively, of the catch element in relation to the pawl. Thus, one may draw conclusions as to the current position of the catch element in relation to the pawl from the current measurement value of the electric component. Accordingly, in turn one may infer, from this determined position of the catch element in relation to the pawl, the number of catches by which the catch element has already moved forward (starting from an initial position) in relation to the pawl, i.e. the number of threshold-value overshoots and/or undershoots that have already taken place. Therefore, it is not only possible to detect the occurrence of a threshold-value event, but the inventive device is also capable of sensing and possibly storing the number of threshold-value overshoots by means of the electric component.

In accordance with one embodiment, the latching mechanism may be configured as a microsystem (MEMS: microelectromechanical system). A MEMS clearly differs from precision-mechanical structures in terms of design and requirements placed upon its production. While precision-mechanical structures, e.g. gearwheels for clockworks, are mostly punched and sometimes lasered, MEMS structures are typically manufactured while using etching processes. Many structures that can be manufactured in precision engineering are very difficult or impossible to implement in MEMS technology. However, manufacturing the latching mechanism as a MEMS yields the decisive advantage that the latching mechanism becomes very compact and involves little space. Particularly in comparison with the above-mentioned precision-engineering structures, MEMS structures are often smaller by factors of several powers of ten.

It is feasible for the inventive device to further comprise a substrate on which the latching mechanism is provided as a MEMS, and wherein deflection of the actuation means is effected within a plane horizontal to the substrate plane. That plane which is demarcated, or spanned, by the lateral outer edges of the substrate is referred to as the substrate plane. With a wafer, for example, the substrate plane is to be more or less equated with the wafer itself, which is flat per se. A movement within a plane parallel to the substrate plane may be, e.g., a movement within or on the substrate provided that the movement means moves in parallel with the substrate plane.

Alternatively, it would also be feasible for the device to comprise a substrate on which the latching mechanism is provided as a MEMS, and wherein deflection of the actuation means takes place perpendicularly to the substrate plane, and wherein the device further comprises a diverting device by means of which the deflection movement of the actuation means, which is directed perpendicularly to the substrate plane, may be diverted to a movement that is directed horizontally to the substrate plane. A movement perpendicular to the substrate plane would be, e.g., a movement of the actuation means out of the substrate plane, i.e. the actuation means would move away from the substrate perpendicularly, for example. A corresponding diverting device may be provided, for example, in the form of gearwheels, in particular bevel gears or worm gears. However, it would also be feasible for the diverting device to comprise first and second diverting means, the first diverting means comprising an oblique face and the second diverting means being in contact with this oblique face. When the second diverting means exerts pressure onto the oblique face, the first diverting means will move in a direction that is oblique to the direction of movement of the second diverting means. For example, with an oblique face having an angle of 45°, diversion of a horizontal to a vertical movement may be implemented. In this case, actuation of the pawl and/or of the catch element is not effected directly by the actuation means but indirectly by the interposed diverting device. This means that the actuation means actuates the diverting device (perpendicularly to the substrate plane), and the diverting device actuates the pawl and/or the catch element (horizontally to the substrate plane).

In accordance with one embodiment, the catches are arranged one behind the other along the catch element in the freewheeling direction, so that the pawl will consecutively engage, in the catch-wise movement, from one catch interstice into the respectively next adjacent catch interstice. This distinguishes the inventive device from other devices which comprise only one catch element having one single catch and one pawl. While a resetting mechanism may be used with such systems after actuation has taken place, in the inventive device the catch element may be moved several times in relation to the pawl.

Also, it is conceivable for the catch element to be a freely rotatable gearwheel wherein the catches are configured in the form of a toothing arranged radially on the outside or on the inside of the gearwheel. Such a gearwheel is relatively easy to manufacture also in MEMS technology. Moreover, configuration of the catch element as a gearwheel has the advantage that the gearwheel may be moved on (catch-by-catch) infinitely, as it were, in relation to the pawl. However, it is also feasible for an end stop to be provided which limits the number of catch-wise movements. For example, the end stop might limit further rotation of the gearwheel once the gearwheel has completed a full revolution. Thus, one may avoid that a counter circuit connected to the gearwheel is reset to zero once a revolution by 360° has been performed. Therefore, this would have the advantage that—e.g. with a gearwheel, which, as was mentioned above, theoretically can be infinitely rotated—the end stop is configured such that the gearwheel rotates by 360° one single time at the most. In this manner, it can be ensured that there are no overlaps in reading the meter. This means that each position of the gearwheel can be taken up one single time only because of the end stop at 360°. Thus, a value of the electric component which is associated with a specific position of the gearwheel can also only be produced once and is therefore unique. Thus, no ambiguities may occur. However, an end stop may also be used with racks and the like so as not to exceed a specific number of catch-wise movements.

It would also be feasible for the catch element, in this case the gearwheel, which is driven by the drive mechanism, to in turn engage in further elements, e.g. further gearwheels, so that a gear unit results. With corresponding toothing (gear reduction), the catch element may thus be rotated by more than 360°, whereas the further element linked to the electric component will then rotate by less than 360° and take up a unique position.

Likewise, would be feasible for the catch element to be a rack that is movable in relation to the pawl and wherein the catches are configured in the form of a toothing arranged on the rack. A rack may have a linear or a curved shape, for example. With a curved shape, the toothing may be arranged on the inside, i.e. directed toward the center of the curvature radius, and/or on the outside, i.e. on that side of the rack that faces away from the center of the curvature radius.

It is conceivable for the actuation means to actuate the catch element to move the catch element further by one catch, respectively, on a catch-by-catch basis in relation to the pawl in the freewheeling direction. As was already mentioned above, the actuation means may actuate the catch element directly or indirectly. Actuation of the catch element has the advantage that the pawl may be arranged to be stationary on the device while the catch element is moved in the freewheeling direction. Jumping from one catch interstice to the next catch interstice in the freewheeling direction on the part of the pawl on a catch-by-catch basis may here be effected, for example, by means of suitable shaping of the catches and of the pawl, so that the pawl, when the catch element is moving, glides across the catch along the catch edge and latches into the adjacent catch interstice.

The actuation means will suitably act upon a catch of the catch element so as to move the catch element further, on a catch-by-catch basis, in relation to the pawl. Thus, the actuation means may act upon a tooth of a gearwheel, for example, and may move the gearwheel forward directly by one tooth. This is a relatively simple possibility of actuating the catch element since no further pivot arms etc. are required.

It would also be feasible for the catch element to be biased by means of a tensioning element and/or for the actuation means to actuate the pawl; upon a movement of the pawl, which releases the engagement with a catch interstice, the biased catch element is moved forward by one catch in each case due to the bias before the pawl engages in an adjacent next catch interstice of the catch element again. This would be roughly comparable to an escapement in a clockwork. This would have the advantage that, e.g. with a gearwheel, which can theoretically be turned on continuously, as was mentioned above, the bias is selected to be such that the gearwheel rotates by 360° only one single time at the most. Specifically, in this way one can ensure that there will be no overlaps in reading the meter. This means that each position of the gearwheel can be taken up one single time only because of the bias. Thus, a value of the electric component, which is associated with a specific position of the gearwheel, can also only be produced once and is therefore unique. Ambiguities are therefore excluded. Alternatively or additionally, provision of an above-mentioned end stop would be feasible here, too.

It is conceivable for the actuation means to be thermally deflectable. Thus, thermal threshold-value overshoots can be measured.

In this context, the actuation means might be a thermal bending transducer, or the actuation means may comprise a shape memory alloy. A thermal bending transducer is understood to be a component which changes its shape as a function of the temperature. The thermal bending transducer may deform toward a first direction once a threshold-value temperature has been exceeded, for example. When this threshold-value temperature is fallen below, the thermal ending transducer will return to its initial position, i.e. it will deform toward the other direction again. A thermal bending transducer may also be a component known by the name of bimorph among English speakers. Such a bimorph comprises two or more active areas that may be actuated separately from one another. A thermal bimorph comprises two active areas, for example, which will deform toward a first direction once a threshold-value temperature is exceeded. When said threshold-value temperature is fallen below, the two active areas will move back into their initial positions, i.e. toward an opposite second direction. Both active areas may have different coefficients of temperature expansion. As a result, the extent of deformation of both active areas will differ, which in turn will result in mechanical deflection of the bimorph. The thermal bimorph may thus move in two directions in response to a threshold-value temperature being fallen below and/or exceeded.

Alternatively or additionally, the actuation means may be mechanically or electrically deflectable. For example, the actuation means may be mechanically deflectable when certain forces, e.g. pressure, apply. This may be a barometric pressure, for example, i.e. the actuation means may be employed in diving chronographs, for example, and indicate the number of dives. However, the actuation means may also be deflectable by acceleration forces, for example. In this manner one may identify whether and how often a device has fallen down from a specific height, or the number of speeding occurrences in vehicles can be identified.

It is feasible for the actuation means to be configured to be deflected once a predefined threshold value is exceeded and/or fallen below so as to move, by means of said deflection, the catch element and the pawl in relation to each other in the freewheeling direction. Depending on the force (e.g. thermal, electrical, mechanical) by which the actuation means is deflectable, such a threshold value may be, e.g., a predefined amount of a temperature, of a pressure, of an acceleration or of different thermal, electrical or mechanical forces. Said threshold value may be both an upper and a lower threshold value. At any rate, the actuation means will, according to the invention, actuate the pawl and/or the catch element only when the force which deflects the actuation means falls below or exceeds the threshold value. This means that it will only be when the predefined threshold value is fallen below or exceeded that the deflection of the actuation means will be sufficient to move the catch element and the pawl relative to each other.

In accordance with a feasible embodiment, the electric component may be a capacitor or a resistor or a coil or an electro-optical element. All these electric components are suitable for noticing even very small changes in their respective electrical behavior.

It would be feasible, for example, for the electric component to be an adjustable member of an RFID resonant circuit. Thus, the electric component might be, e.g., an electrical load with a variable resistance, a capacitor with variable capacitance, or a coil with variable inductance, their respective electric properties varying as a function of the quantity to be determined (e.g. temperature, pressure, etc.). As the electric property changes, the resonant frequency of the entire RFID resonant circuit will also change. Thus, the (active or passive) RFID resonant circuit may be read out by using an RFID reader, for example; the frequency of the resonant circuit may be an indicator of the current value of the respective adjustable electric component and may thus simultaneously also be an indicator of the current position of the catch element in relation to the pawl.

It is feasible for the device to comprise a substrate which has the latching mechanism arranged thereon and wherein the electric component is arranged between the latching mechanism and the substrate. Thus, displacing of the catch element in relation to the substrate may result in a change of the electric property of the electric component. Also, this arrangement is space-saving since the electric component may be integrated directly into the substrate, for example, and may thus be arranged directly below the catch element rather than next to it.

In accordance with an embodiment of the invention, the device may comprise a substrate which has the latching mechanism arranged thereon, and the electric component may be a capacitor, a first capacitor plate being provided at the substrate, and a second capacitor plate being provided at the catch element and/or at the pawl, and the alignment of the capacitor plates in relation to each other changing upon a catch-wise movement of the catch element and/or of the pawl in relation to the substrate, so that the capacitance of the capacitor will change.

The inventive device may be configured as a counter of sterilization cycles, for example, wherein the actuation means shifts, with each sterilization process, the catch element and the pawl by one catch, respectively, in relation to each other in the freewheeling direction.

BRIEF DESCRIPTION OF THE DRAWINGS

Embodiments of the present invention will be detailed subsequently referring to the appended drawings, in which.

DETAILED DESCRIPTION OF THE INVENTION

Figure 1:
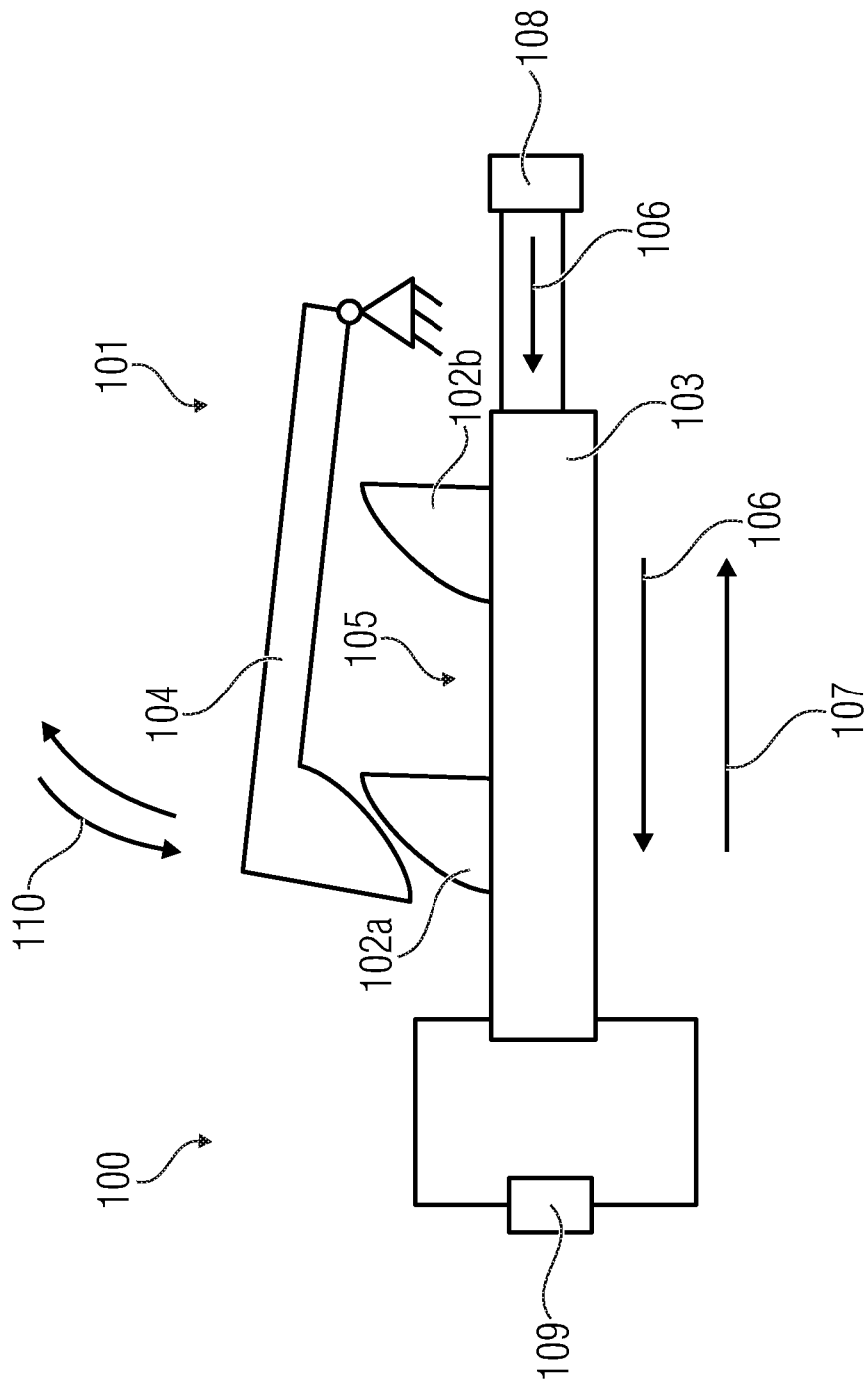
FIG. 1 shows a schematic side view of an embodiment of an inventive device.

FIG. 1 shows a schematic picture of an inventive device 100. The device 100 comprises a latching mechanism 101. The latching mechanism 101 comprises a catch element 103 and a pawl 104. The catch element 103 comprises at least two catches 102a, 102b. The two catches 102a, 102b have a catch interstice 105 formed between them into which the pawl 104 may engage.

In a freewheeling direction 106, the catch element 103 is movable in relation to the pawl 104. However, in a blocking direction 107, a movement of the catch element 103 in relation to the pawl 104 may be blocked by means of the pawl 104. This may be implemented, for example, by suitable shapes, shown in FIG. 1, of the pawl 104 and of the individual catches 102a, 102b.

The catch 102a has a rounded side and a flat side. The pawl 104 also comprises a rounded side and a flat side. While in the freewheeling direction 106, the two rounded sides glide across each other, the respectively flat side block a movement of the pawl 104 in relation to the catch 102a in the blocking direction 107.

A relative movement of the catch element 103 and of the pawl 104 in relation to each other is understood to be a movement of the two elements 103, 104 in relation to each other in the freewheeling direction 106, i.e. displacement of the two elements 103, 104 in relation to each other. The movement of the pawl 104 upon engagement in the catch interstice 105 and the movement upon release of the engagement typically is an upward and downward movement 110 that is transverse to the freewheeling direction 106. This upward and downward movement 110 of the pawl 104, however, is not what is meant, as defined by the present disclosure, by the relative movement, indicated in the description, between the catch element 103 and the pawl 104.

The inventive device 100 further comprises deflectable actuation means 108. The actuation means 108 is configured to move the catch element 103 and the pawl 104 relative to each other on a catch-by-catch basis in the freewheeling direction 106 by means of deflection.

In the embodiment depicted in FIG. 1, the actuation means 108 is a linear actuator which may be deflected linearly along and/or in parallel with the freewheeling direction 106. By means of this deflection movement, the actuation means 108 in this case actuates the catch element 103 and pushes it forward, on a catch-by-catch basis, in relation to the pawl 104. However, it is also feasible for the actuation means 108 to actuate the pawl 104 by means of a suitable deflection movement. Such an embodiment will be explained in more detail below with reference to FIGS. 5 and 6.

What generally applies to all embodiments is that the deflectable actuation means 108 may also move, or actuate, the pawl 104 and/or the catch element 103 by means of a pivoting movement, for example. It would be feasible, for example, for the actuation means 108 to be configured to deform (e.g. upon external energy such as thermal and/or electrical and/or mechanical energy being supplied, for example) and to move, or actuate, the pawl 104 or the catch element 103 during the deformation process. Such embodiments will be explained below in more detail with reference to FIGS. 2, 3A to 3F, 6, 7A to 7C, 9, 10, and 11A to 11D.

The inventive device 100 further comprises an electric component 109. The electric component 109 is configured to change its electric property as a function of the catch-wise movement of the catch element 103 in relation to the pawl 104. In the embodiment depicted in FIG. 1, the electric component 105 changes its electric property each time the actuation means 108 pushes the catch element 103 further by one catch 102a, 102b.

The electric component 109 may be a variable ohmic resistor, for example, which changes its resistance as a function of the position of the catch element 103 in relation to the pawl 104. However, the electric component 109 may also be a capacitor which changes its capacitance as a function of the position of the catch element 103 in relation to the pawl 104. It would also be feasible for the electric component 109 to be a coil which changes its inductance as a function of the position of the catch element 103 in relation to the pawl 104.

Figure 2:
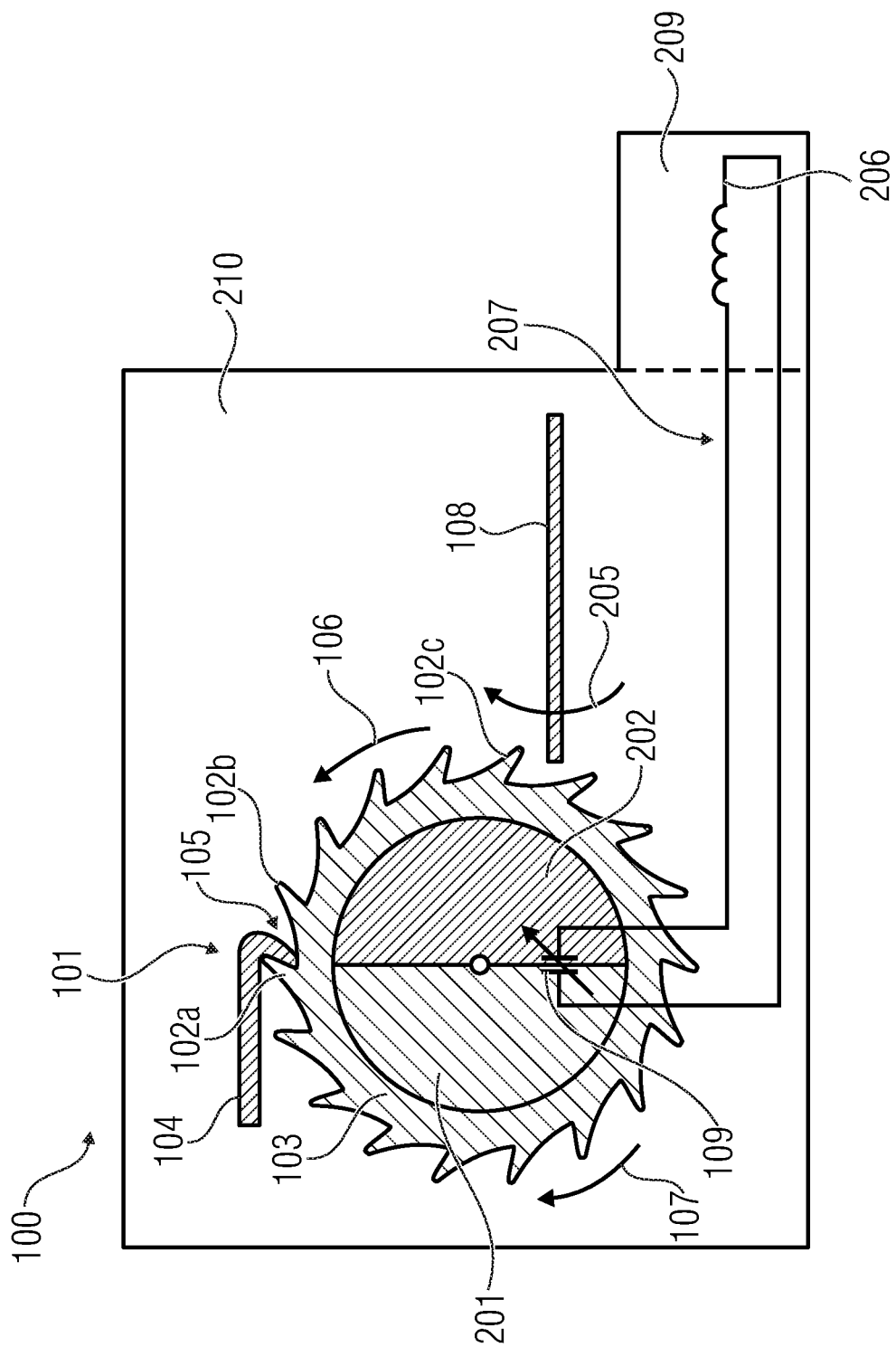
FIG. 2 shows a schematic side view of a further embodiment of an inventive device.

FIG. 2 shows a further embodiment of an inventive device 100. Here, too, the latching mechanism 101 comprises a pawl 104 and a catch element 103 having at least two catches 102a, 102b; the pawl 104 may engage in a catch interstice 105 between the two catches 102a, 102b.

The catch element 103 here is configured as a gearwheel. The individual catches 102a, 102b are configured in the form of a toothing arranged radially on the outside of the gearwheel 103. However, it would also be feasible for the individual teeth 102a, 102b to be configured in the form of a toothing that is arranged radially on the inside of the gearwheel 103.

The gearwheel 103 here is configured as a freely rotatable gearwheel. However, it would also be feasible for the gearwheel 103 to be elastically rotatable, i.e. the gearwheel 103 might be rotatable counter to a spring force, for example. A spring (not depicted here) such as a mainspring known from clockworks, for example, might be coupled to the gearwheel 103 so that the spring will become stressed (i.e. will undergo either compressive stress or tensile stress) when the gearwheel 103 is moved in a first direction, and so that the spring will become destressed when the gearwheel 103 is moved in a second direction that is opposite to the first direction.

In the freely rotatable gearwheel 103 as shown in FIG. 2, the pawl 104 engages in the tooth interstices 105 between two teeth 102a, 102b of the gearwheel 103. One can see that here, too, because of the specific shape of the pawl 104 and of the individual teeth 102a, 102b of the gearwheel 103, a freewheeling direction 106 results in which the gearwheel 103 is freely rotatable in relation to the pawl 104. In the opposite direction, i.e. in a blocking direction 107, however, the pawl 104 will block the movement of the gearwheel 103.

In this embodiment, the actuation means 108 actuates the catch element 103 so as to move the catch element 103 further, in relation to the pawl 104, in the freewheeling direction 106 by one catch 102a, 102b, in each case, on a catch-by-catch basis. As can be seen, the actuation means 108 here acts on a catch 102c of the catch element 103 so as to move the catch element 103 further in relation to the pawl 104 on a catch-by-catch basis.

The inventive device 100 here is provided on a substrate 210. The substrate 210 may be a silicon wafer, for example. The inventive device 100 may be provided on the substrate 210 as a MEMS (micro-electromechanical system). For example, the depicted gearwheel structure 103 may be manufactured by means of suitable etching processes.

As is indicated by the arrow 205, the actuation means 108 is deflected upward within the image plane so as to actuate the gearwheel 103. Deflection of the actuation means 108 thus takes place within the substrate plane, i.e. within a plane that is parallel and/or horizontal to the substrate plane.

The movement of the actuation means 108 essentially is a pivoting movement caused by external energy (e.g. thermal energy) being supplied, the behavior of the actuation means 108 being roughly comparable to that of a cantilevered bending beam.

The electric component 109 is configured as a capacitor here. More specifically, a first capacitor plate 201 is provided at the substrate 210, and a second capacitor plate 202 is provided at the catch element 103.

As can be seen, the two capacitor plates 201, 202 are two semicircular segments. In the position, shown in FIG. 2, of the gearwheel 103 in relation to the substrate 210, the two capacitor plates 201, 202 are mutually aligned such that they are located exactly opposite each other, i.e. so that they merge to form a complete circle when viewed from the top.

Because of the positions of the two capacitor plates 201, 202 in relation to each other, the capacitor 109 in this position has a specific capacitor capacitance. When the catch element 103 is moved, on a catch-by-catch basis, in relation to the substrate 210, the gearwheel 103 will rotate in relation to the substrate 210, and therefore, the alignment of the two capacitor plates 201, 202 in relation to each other will change. At the same time, the capacitor capacitance of the capacitor 109 will also change.

In the embodiment depicted in FIG. 2, the electric component, i.e. the capacitor 109, is an adjustable member of an RFID resonant circuit 207. The RFID resonant circuit 207 also comprises a coil 206 in addition to the capacitor 109. What is at hand here, therefore, is an LC circuit having a resonant frequency that depends on the component.

The resonant frequency of the resonant circuit 207 changes as a function of the capacitor capacitance of the adjustable capacitor 109. For example, each position of the gearwheel 103 in relation to the substrate 210 and/or in relation to the pawl 104 results in a specific position of the two capacitor plates 201, 202 in relation to each other. This results in a specific capacitor capacitance and, thus, a specific resonant frequency of the RFID resonant circuit 207 for each position.

This means that the RFID resonant circuit 207 has a specific resonant frequency for each position of the gearwheel 103 in relation to the substrate 210 and/or in relation to the pawl 104. The RFID resonant circuit 207 may be read out by means of a suitable RFID reader. In this context, therefore, one may infer the position of the gearwheel 103 (second capacitor plate 202) in relation to the substrate 210 (first capacitor plate 201) and/or in relation to the pawl 104 from the respectively characteristic transmission frequency of the resonant circuit 207.

For this purpose, the device 100 may have an electronic interface 209. The electronic interface 209 need not necessarily be part of the MEMS element itself. The electronic interface 209 enables reading out the change in the electric component 109, e.g. when the electric component 109 directly represents the adjustable member of an RFID resonant circuit or of more sophisticated electronics.

Therefore, if the electric component 109 corresponds to a typical element (capacitor, coil, resistor) of a resonant circuit 207, e.g. to a variable capacitor 109, and if the latter forms an LC circuit 207 together with a coil structure 206, a change in the capacitance will also change the resonant characteristics of the resonant circuit 207. The resultant passive transponder of an RFID system (radio-frequency identification) may be read out in a wireless manner by means of a corresponding reading device.

If the electronic component 109 forms part of an electronic circuit, which in turn forms part of an RFID transponder system, electrical energy may be wirelessly coupled into the circuit by means of a corresponding reading device and may be used for performing functions of the electronic circuit, e.g. for signal amplification, signal evaluation and further transmission tasks.

FIGS. 3A to 3F show detailed views of a deflection of the actuation means 108 and of associated actuation of the gearwheel 103 depicted in FIG. 2 in relation to the substrate 210 and/or in relation to the pawl 104.

Figure 3A:
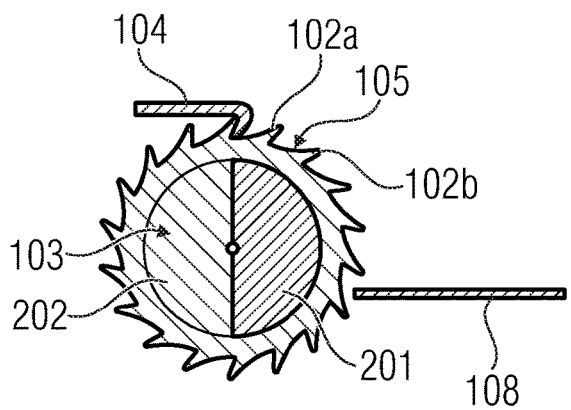
FIGS. 3A-3F show detailed views for describing the mode of operation of the inventive device.

FIG. 3A shows the latching mechanism 101 comprising the pawl 104 and the gearwheel 103 as well as the actuation means 108 in an initial position. All elements 103, 104, 108 are largely at rest.

Figure 3B:
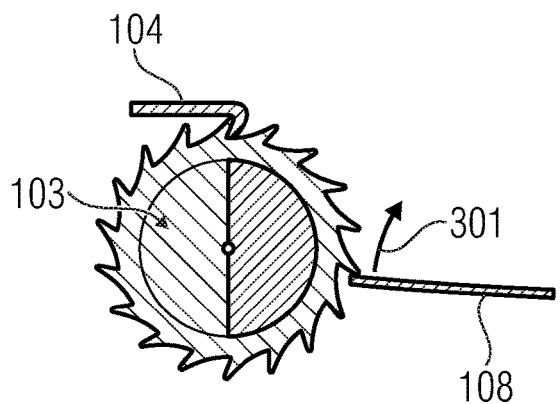

FIG. 3B shows how the actuation means 108 starts to move. The actuation means 108 is deflected upward within the image plane, i.e. is deflected along the direction symbolized by the arrow 301. In this context, the actuation means 108 touches, in portions, one of the teeth of the gearwheel 103 and comes to abut with same.

Figure 3C:
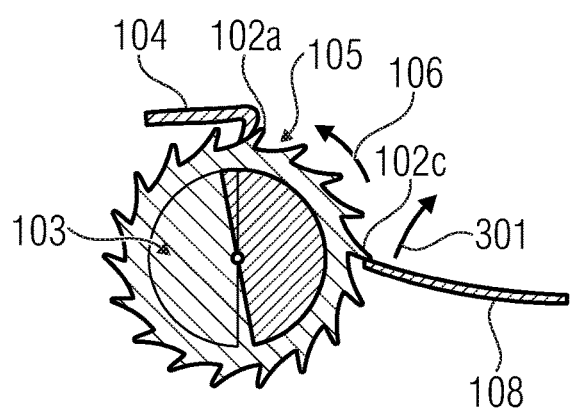

FIG. 3C shows how the actuation means 108 is further deflected upward in the direction of the arrow 301. In this context, the actuation means 108 takes along the gearwheel 103 by acting on that tooth 102c of the gearwheel 103 which is engaged with the actuation means 108. The gearwheel 103 starts to rotate in the freewheeling direction 106, and the pawl 104 slides along the tooth flank of the tooth 102, so that the pawl 104 is lifted upward.

Figure 3D:
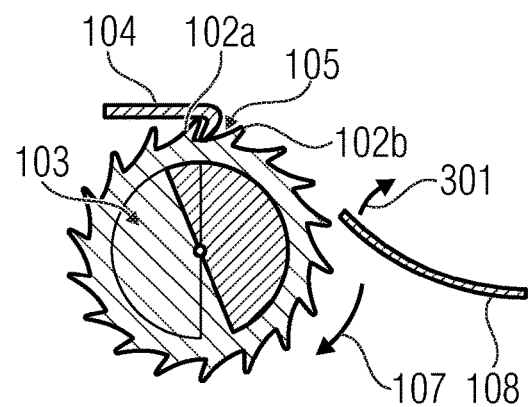

FIG. 3D shows that the actuation means 108 keeps moving upward, i.e. in the direction of the arrow 301, so as to therefore rotate the gearwheel 103 further. Upon further rotation of the gearwheel 103, the pawl 104 slides across the tooth 102a and engages in the next tooth interstice 105 between the teeth 102a and 102b. The pawl 104 now blocks a backward movement of the gearwheel 103 in the blocking direction 107.

Figure 3E:
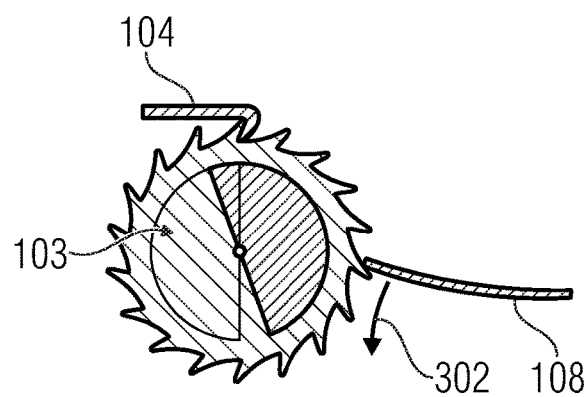

As can be seen in FIG. 3E, the actuation means 108 now moves back into its initial position again. In the process, the actuation means 108 is deflected again in the opposite direction, depicted by arrow 302, i.e. downward within the image plane. In the process, the actuation means 108 slides across the teeth of the gearwheel 103 since the gearwheel 103 is secured, by means of the pawl 104, against rotating in the blocking direction 107.

Figure 3F:
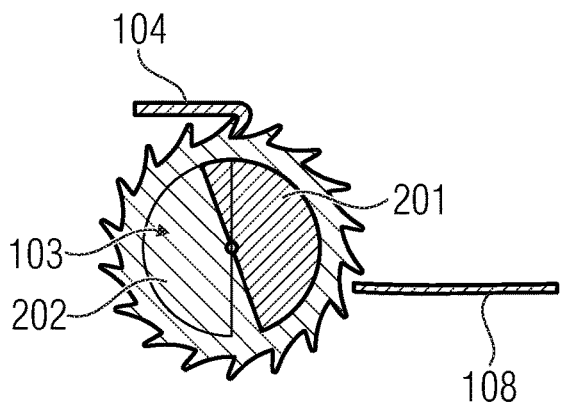

One can see in FIG. 3F that the actuation means 108 has returned into its initial position. The actuation means 108 may engage, upon its next deflection in the direction of the arrow 301, in the next tooth of the gearwheel 103 and rotate the gearwheel 103 further again by one tooth in the above-described manner. The mechanism described which consists of the actuation means 108, the catch element 103 and the pawl 104 is configured, in accordance with the invention, such that the catch element 103 is moved further, in relation to the pawl 104, only in a catch-by-catch manner, i.e. only by one catch at a time.

One can also see in FIG. 3F how the first capacitor plate 201 arranged at the gearwheel 103 is displaced in relation to the second capacitor plate 202 provided within the substrate 210. As a result, the capacitance of the capacitor changes as compared to the initial position shown in FIG. 3A.

In the embodiment shown in FIGS. 3A to 3F, both capacitor plates 201, 202 are mutually arranged such that they do not superimpose, or overlap, each other in the initial position shown in FIG. 3A. As compared to all of the other positions the gearwheel 103 might possibly take up, the capacitance of the capacitor here has the lowest value, i.e. the capacitance here is about zero. As the rotation of the gearwheel 103 increases, the overlap of the two capacitor plates 201, 202 also increases, so that the capacitance of the capacitor keeps rising. With a rotation of 180°, the two capacitor plates 201, 202 fully overlap, so that the capacitor 109 in this position exhibits the largest amount of capacitance as compared to any other positions the gearwheel 103 might take up. As the rotation of the gearwheel 103 continues, the capacitance of the capacitor decreases again.

The capacitor plates 201, 202 here are configured as semicircular plates, but other suitable shapes would also be feasible.

The movement of the actuation means 108 essentially is a pivoting movement caused by supplying external energy (e.g. thermal energy), the behavior of the actuation means 108 being roughly comparable to that of a cantilevered bending beam.

The electric component 109 need not necessarily be a capacitor. It would also be feasible for the electric component 109 to be an ohmic resistor, a coil or an electro-optical element.

Figure 4:
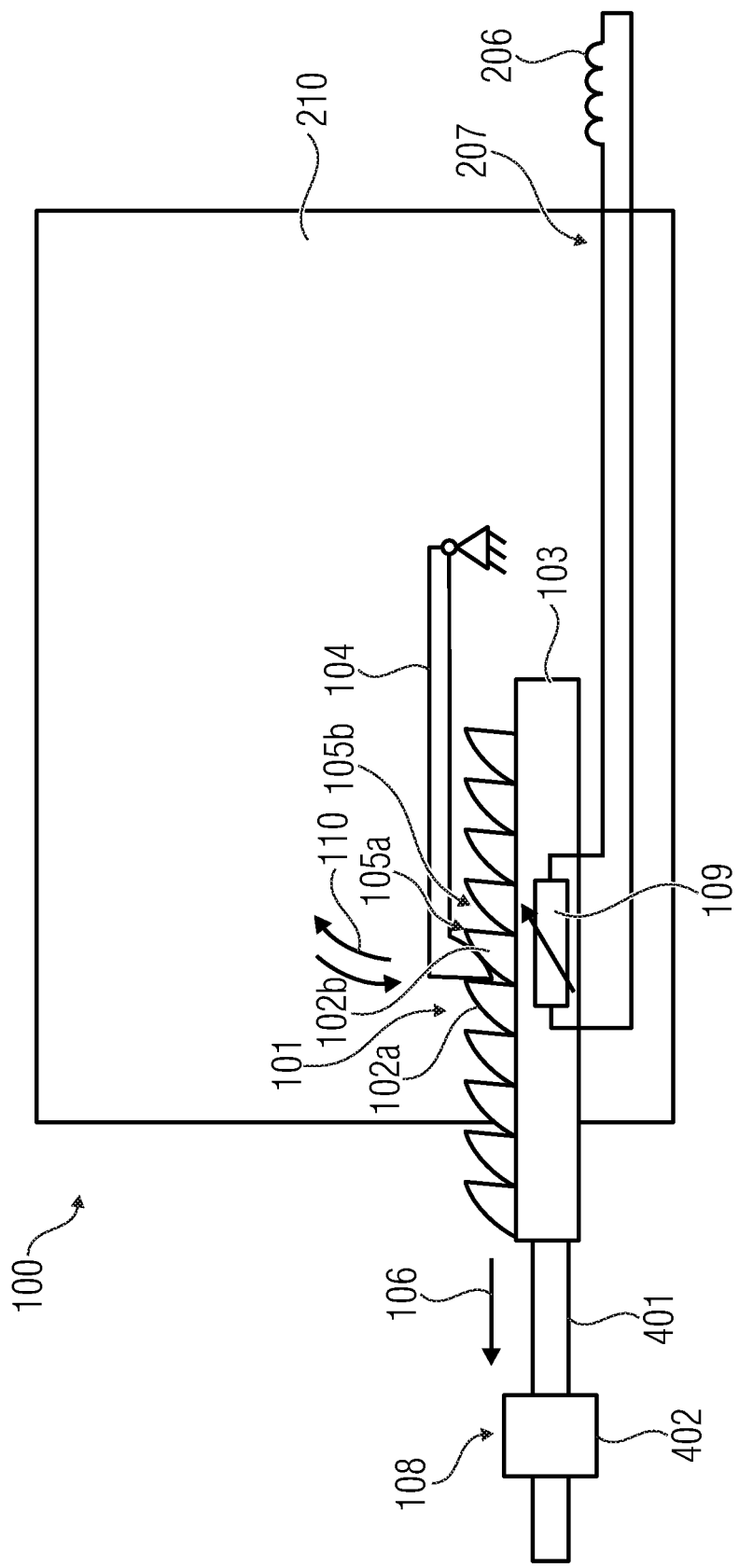
FIG. 4 shows a schematic side view of a further embodiment of an inventive device.

An embodiment where an ohmic resistor would be suitable, for example, is shown in FIG. 4. The setup of the inventive device 100 depicted here is similar to the example of FIG. 1. Here, too, a latching mechanism 101 is arranged on a substrate 210. In addition, the actuation means 108 is also configured as a linear actuator which actuates the catch element 103.

The catch element 103 here is configured as a rack comprising several teeth. In contrast to the example shown in FIG. 1, however, the actuation element 103 does not push the rack 103 in the freewheeling direction 106, but the rack 103 is drawn in the freewheeling direction 106 by the actuation means 108.

With each pulling further of the rack 103 by the actuation means 108 on a catch-by-catch basis, the pawl 104 moves up and down along the directions shown by the arrows 110 so as to engage in the respective tooth interstice 105a between the individual teeth 102a, 102b.

The catch element 103 here is depicted as a linear rack. However, it is also feasible for the rack 103 to be curved rather than being linear. For example, a rack 103 may have a structure in the shape of a circular arc or a circular segment, wherein the toothing may be arranged radially on the inside and/or radially on the outside.

Irrespective of whether the catch element 103 is a rack or, as depicted in FIG. 2, a freely movable gearwheel, the individual catches 102a, 102b are arranged one behind the other, according to the invention, along the catch element 103 in the freewheeling direction 106, so that the pawl 104 will consecutively engage, in the catch-wise movement, from one catch interstice 105a into the respectively next adjacent catch interstice 105b. As a result, no separate resetting mechanism, as may be used in conventional technology, need be provided in the infinitely rotating gearwheel 103, for example.

The actuation means 108 may comprise, e.g., traction means 401 as well as a traction device 402 which actuates the actuation element 103 by means of the traction means 401. In accordance with embodiments of the invention, the actuation means 108 may be mechanically (this includes thermally) or electrically deflectable, for example.

As was mentioned at the outset, the electric component 109 may be a variable ohmic resistor. In the embodiment shown here, the resistor 109 is arranged between the latching mechanism 101 and the substrate 210. The variable ohmic resistor 109 is roughly comparable to a potentiometer. With each catch-wise onward movement of the catch element 103 in relation to the pawl 104 and/or to the substrate 210, its electric resistance changes.

The ohmic resistor 109 may also be part of a resonant circuit 207. What is at hand here, for example, is a tunable RL circuit 207 comprising the mentioned ohmic resistor 109 as well as a coil arrangement 206.

In this embodiment, too, a capacitor may be employed, instead of the ohmic resistor, as a tunable electric component 109 so as to form, together with the coil 206, a tunable LC circuit 207 described above with reference to FIG. 2.

As was also mentioned above with reference to FIG. 2, the catch element 103 may be freely movable or may be elastically movable. While FIG. 4 shows a freely movable rack 103, FIG. 5 shows a rack 103 which is biased by means of a spring 501 and is therefore elastically movable.

Figure 5:
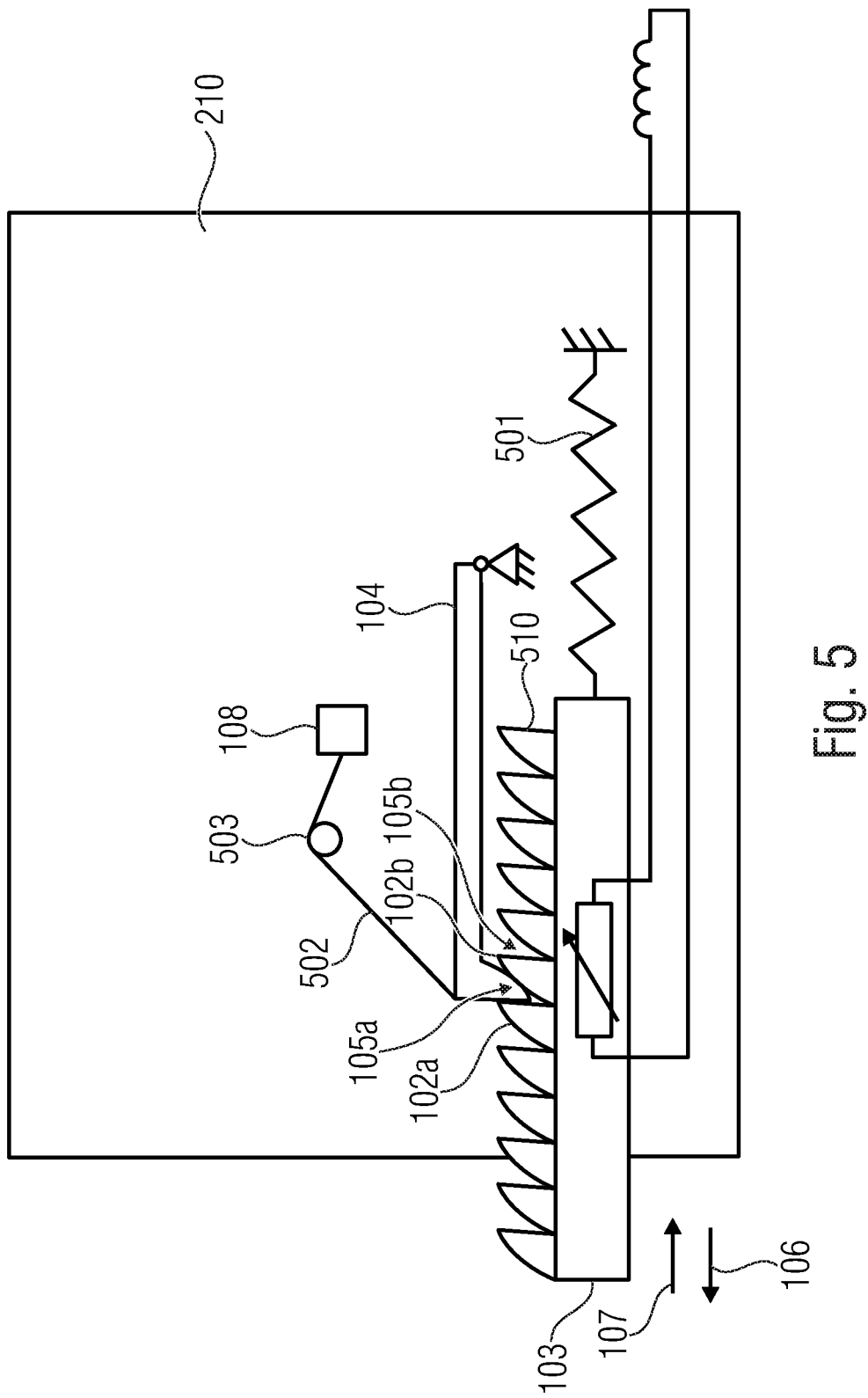
FIG. 5 shows a schematic side view of a further embodiment of an inventive device.

FIG. 5 therefore shows a further embodiment of the inventive device 100. The device 100 depicted here essentially corresponds to the embodiment described above with reference to FIG. 4. However, one difference consists in the fact that the actuation means 108 here actuates the pawl 104 rather than the catch element 103.

The catch element 103 here is biased by means of a tensioning element 501. The tensioning element 501 may be a tension spring, for example, which in the initial state is pulled apart and thus biased. In the example depicted here, the catch element 103 might be wound up to the last tooth 510 in the freewheeling direction 106 (in FIG. 5, the tooth on the extreme right) counter to the tensile force of the tension spring 501. The pawl 104 engages in the last tooth interstice blocks the movement of the catch element 103 in the blocking direction 107.

As was mentioned at the outset, the actuation element 108 actuates the pawl 104. The actuation element 108 here need not directly contact the pawl 104, but the actuation element 108 may also be connected to the pawl 104 via connecting means 502, for example. The actuation element 108 may also optionally comprise a diverting device 503, so that the actuation means 108 need not necessarily move the pawl 104 in the same direction as the deflection direction of the actuation means 108. What was just said evidently also applies to an actuation means 108 which actuates the catch element 103.

As was mentioned at the outset, the catch element 103 therefore is biased by means of the tension spring 501, i.e. the tension spring 501 pulls the catch element 103 in the blocking direction 107. However, the pawl 104 blocks the movement of the catch element 103 in this very blocking direction 107. Upon a movement of the pawl 104 which releases the engagement in a catch interstice 105a, the biased catch element 103 will move because of the bias of the tensioning element 501, i.e. the tension spring 501 now pulls the catch element 103 in the blocking direction 107. This is only possible since the pawl 104 has become detached from the engagement with the catch interstice 105a. According to the invention, however, the catch element 103 pushes itself further by only one catch 102a, 102b at a time before the pawl 104 engages in an adjacent next catch interstice 105b again.

Instead of the tension spring that has just been described, a compressive spring might be provided which pushes the catch element 103 in the blocking direction 107. In this case, however, the compressive spin would become effective on the opposite side of the catch element 103 as compared to FIG. 5.

In order to prevent the catch element 103 from sliding through to the pawl 104 (which temporarily is not engaging) in a non-decelerated manner, a braking device such as a further pawl or a mechanical stop may be provided.

Figure 6:
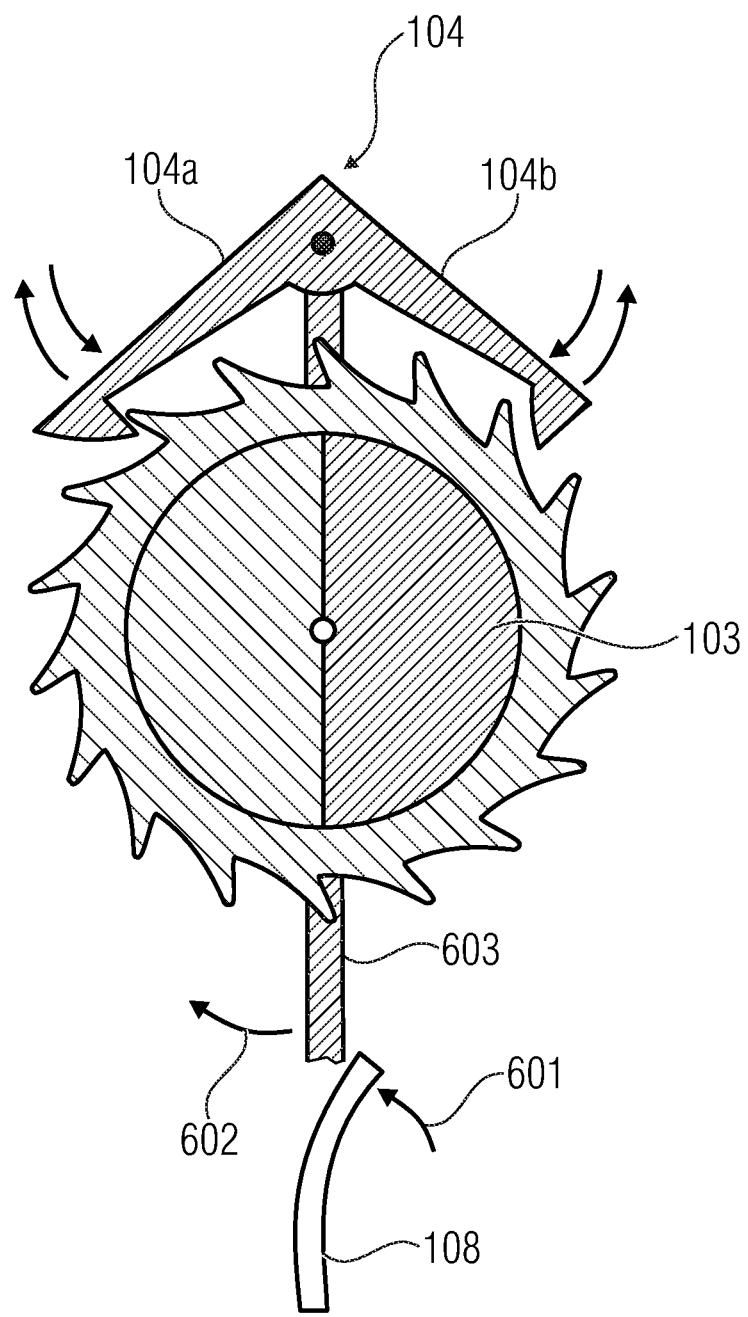
FIG. 6 shows a schematic side view of a further embodiment of an inventive device wherein the actuation means actuates the pawl in accordance with the principle of anchor escapement.

FIG. 6 shows part of such an embodiment where the actuation means 108 actuates the pawl 104. This principle is similar to the principle of anchor escapement as is employed in clockworks, for example. The catch element 103 configured as a gearwheel is biased, e.g. by means of a suitable spring, e.g. by means of a mainspring known from clockworks (not depicted here).

The pawl 104 here is depicted as double pawl here, i.e. it comprises a first, or left, pawl part 104a and a second, or right, pawl part 104b. The pawl 104 is fixed to a bar 603. The actuation means 108 acts on that side of the bar 603 which is located opposite the pawl 104.

Deflection of the actuation means 108 in the direction of the arrow 601 will pivot the bar 603 in the direction of the arrow 602. By means of this pivoting movement, the engagement of the first pawl part 104a in the tooth interstice of the gearwheel 103 is released, and the second pawl part 104b engages in a next adjacent tooth interstice. Between the disengaging and engaging movements of the two pawl parts 104a, 104b, the gearwheel 103 jumps forward by one tooth because it is biased.

Figure 7A:
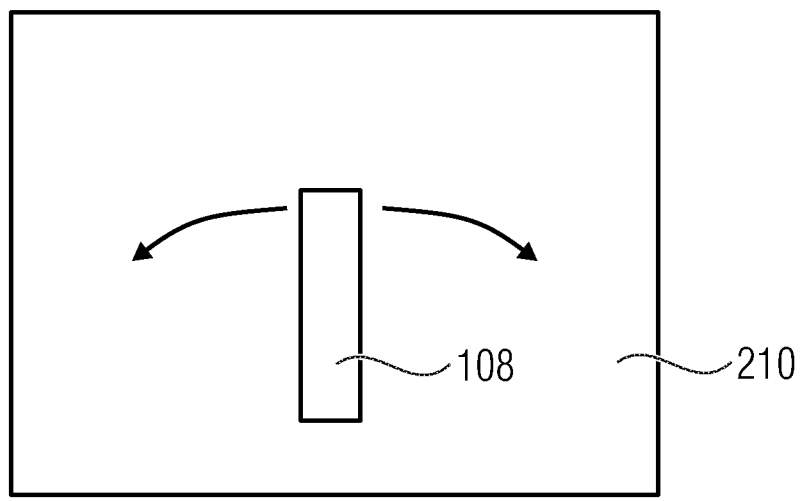
FIG. 7A shows a schematic top view of a substrate comprising an actuation means for visualizing a movement of the actuation means within the substrate plane and/or horizontally to and/or in parallel with the substrate plane.

In all of the above-mentioned embodiments, the movement of the actuation means 108 may be effected within the substrate plane and/or in parallel therewith. FIG. 7A shows a top view of a substrate 210 and an actuation means 108 provided at the substrate 210. As indicated by the arrows, the actuation means 108 may swing out in the directions drawn, for example. This corresponds to a movement within the and/or in parallel with the substrate plane.

Figure 7B:
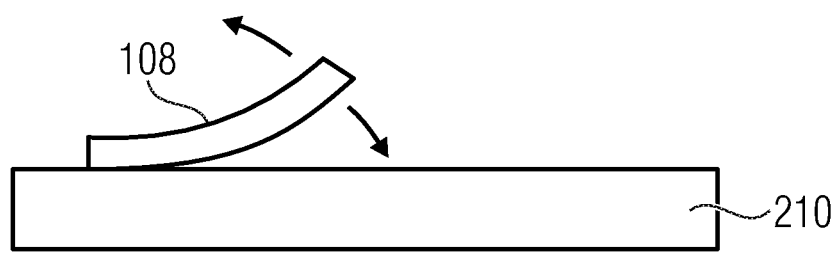
FIG. 7B shows a schematic side view of a substrate comprising an actuation means for visualizing a movement of the actuation means within a plane perpendicular to the substrate plane.

FIG. 7B shows a side view of a substrate 210 and of an actuation means 108. Here, the actuation means 108 moves within a plane perpendicular to the substrate plane.

Figure 7C:
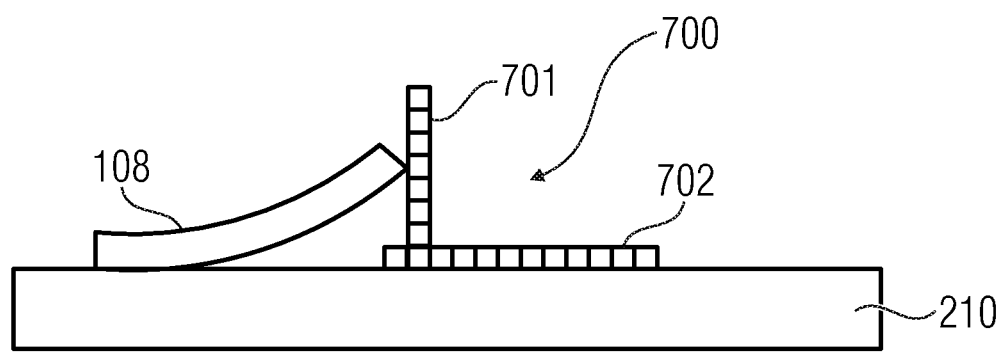
FIG. 7C shows a schematic side view of an inventive device comprising a diverting device.

FIG. 7C shows a further embodiment, wherein a diverting device 700 is provided which is configured to divert the movement of the actuation means 108 within a plane perpendicular to the substrate plane to a movement which in turn is effected within a plane that is horizontal and/or parallel to the substrate plane.

To this end, the diverting device 700 may comprise, e.g., a first gearwheel 701 arranged vertically to the substrate plane and a second gearwheel 702 arranged parallel and/or horizontally to the substrate plane, the two gearwheels 701, 702 intermeshing. The actuation means 108 is deflected and actuates the first gearwheel 701 in the process. The first gearwheel 701 rotates within a plane perpendicular to the substrate plane and, in turn, actuates the second gearwheel 702 in the process. The two gearwheels 701, 702 may engage with each other, for example, by means of a worm/bevel gear toothing system.

Figure 7D:
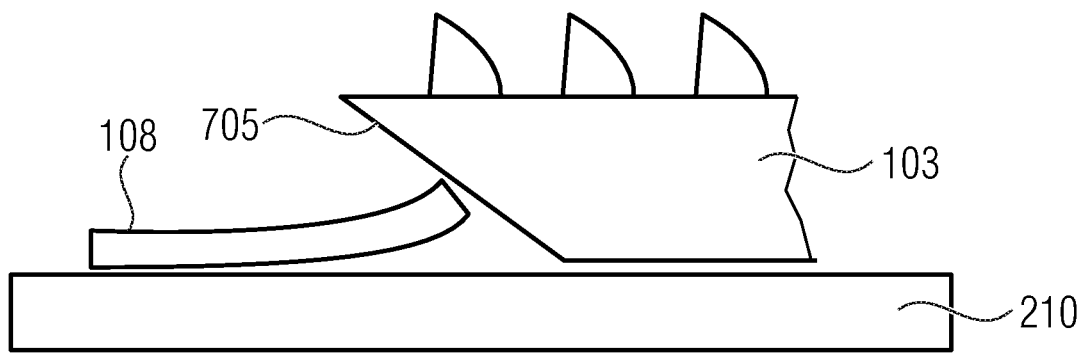
FIG. 7D shows a schematic side view of an inventive device comprising a diverting device in a first state.

FIG. 7D shows a further possibility of implementing a diverting movement by means of microsystem technology. FIG. 7D shows a substrate 210, an actuation means 108 and a catch element 103. The catch element 103 comprises an oblique face 705 which faces the actuation means 108.

Figure 7E:
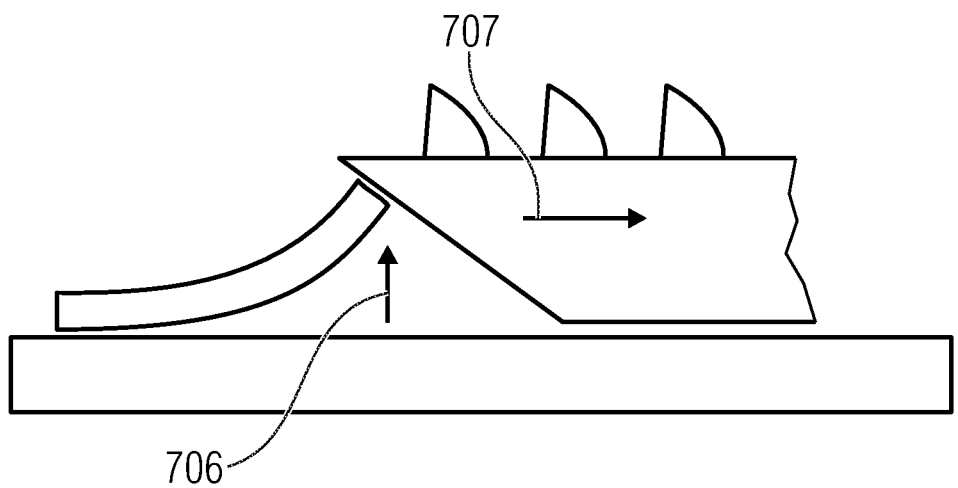
FIG. 7E shows a schematic side view of the inventive device of FIG. 7D in a second state.

FIG. 7E shows how a movement 706 of the actuation means 108 which is directed upward, i.e. is directed perpendicularly to the substrate plane, may result in a movement 107 of the catch element 103 which is directed parallel to the substrate plane. In this context, at least a portion of the actuation means 108 glides along the oblique face 705 of the catch element 103 during the deflection process and thus pushes the actuation means 108 in the direction which is depicted in the arrow direction 107 and is parallel to the substrate plane.

Figure 8:
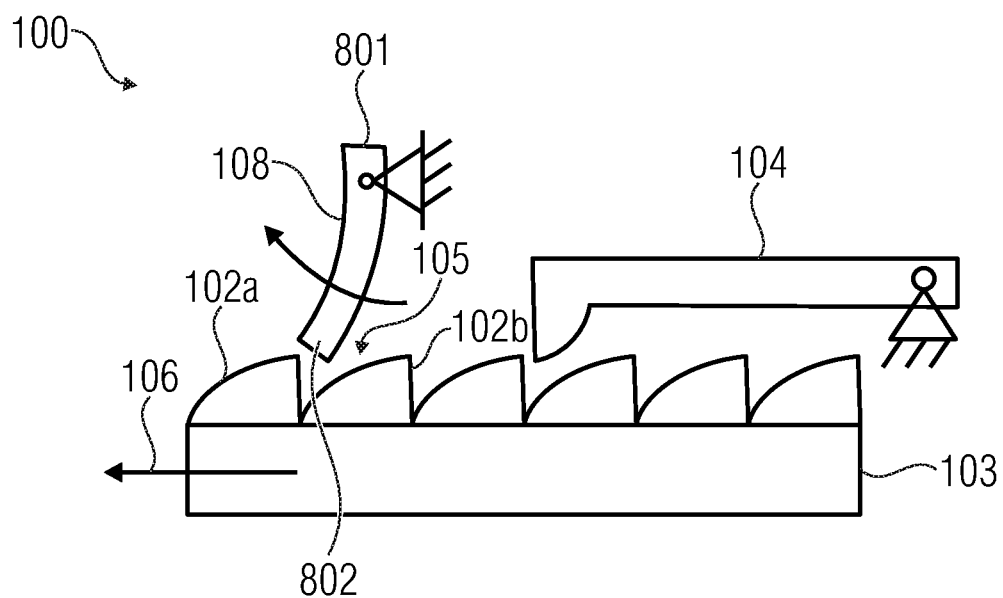
FIG. 8 shows a further embodiment of an inventive device.

FIG. 8 shows a further embodiment of an inventive device 100. The difference as compared to the above-described embodiments consists in that, among other things, the actuation means 108 engages in a catch interstice 105 between two adjacent catches 102a, 102b so as to move forward the catch element 103, configured as a rack, on a catch-by-catch basis.

In actual fact, this device corresponds to the device previously described with reference to FIG. 2, the difference being that the catch element 103 is not a freely rotatable gearwheel but a rack. The rack 103 may also be freely movable or elastically movable, i.e. may be biased by means of a tension spring or compressive spring.

In the embodiment depicted in FIG. 8 it is advantageous for the actuation element 108 to be configured to be roughly perpendicular to the extension direction of the rack 103. As is shown, a bending transducer may thus be employed as the deflectable actuation means 108; that free end 802 of the bending transducer 8 which is located opposite the clamped end 801 engages in the tooth interstice 105.

Figure 9:
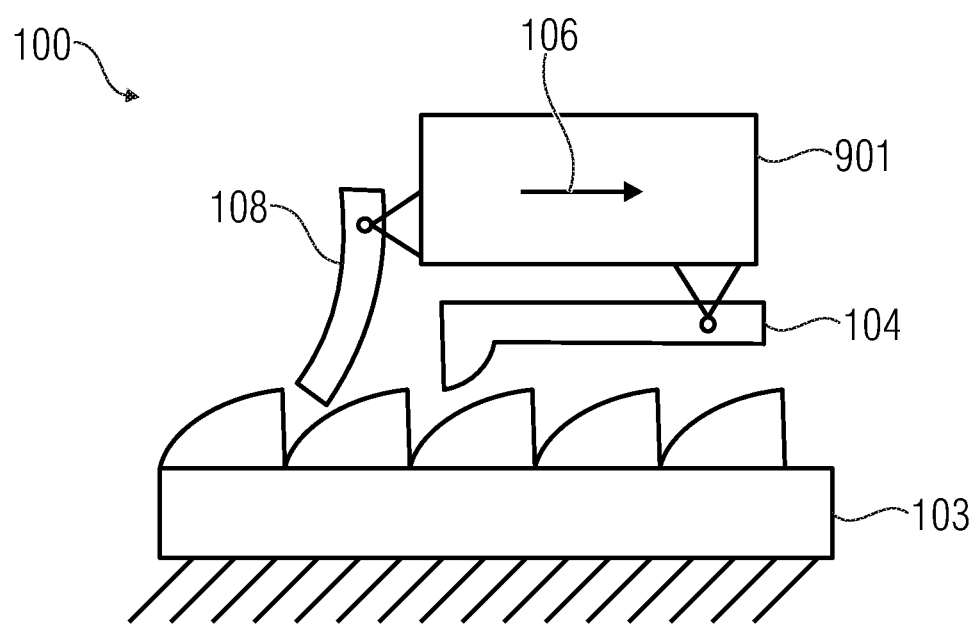
FIG. 9 shows a further embodiment of an inventive device.
Figure 10:
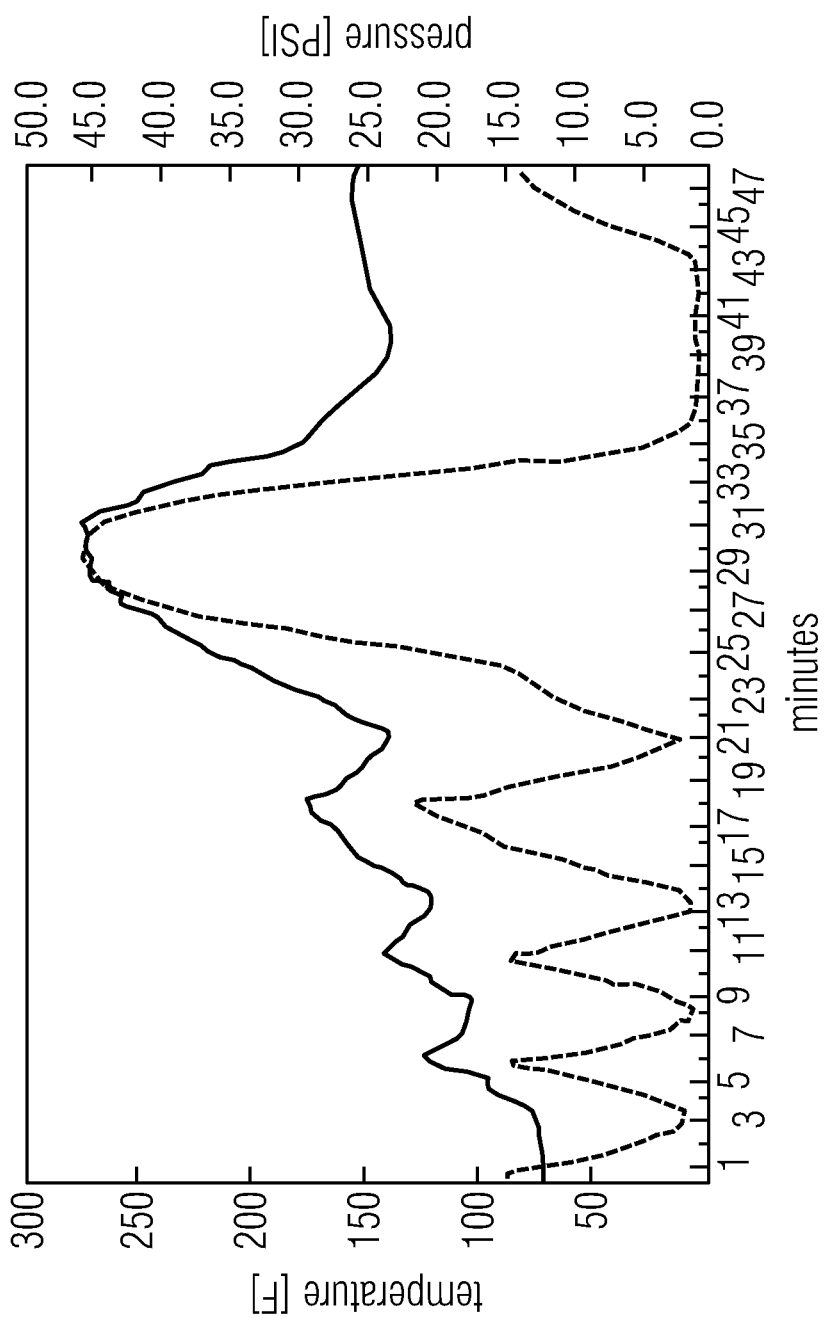
FIG. 10 shows a diagram for visualizing a sterilization cycle.

FIG. 9 shows a further embodiment of an inventive device 100. The difference as compared to the above-described embodiments consists, among other things, in that the catch element 103 is fixed and that both the pawl 104 and the deflectable actuation means 108 are arranged at a device 901 which is movable in relation to the fixed catch element 103. The movable device 901 may be some kind of carriage, for example.

The actuation means 108 is arranged at the movable device 901 and is cantilevered at the movable device 901. The free end of the actuation means 108 engages in a tooth interstice between two adjacent teeth.

The movable device 901 also has the pawl 104 arranged thereat. The pawl 104 is pivotably mounted on the movable device 901, so that the pawl 104 may engage in a tooth interstice and may be swung out of an engagement with a tooth interstice.

A deflection of the deflectable actuation means 108 results in that the free end of the actuation means 108 which is located within a tooth interstice rests on a tooth and moves the movable device 901 in the freewheeling direction 106 in relation to the catch element 103. According to the invention, the catch element 103 is moved forward by one catch only with each deflection process of the actuation means 108. This means that the actuation means 108 pushes the catch element 103 forward by one catch only in each case on a step-by-step basis.

With all of the above-described embodiments, the actuation means 108 may be deflected in different manners. For example, the actuation means 108 may be thermally deflectable. This means that the actuation means 108 may change its shape as a function of the temperature.

For example, the actuation means 108 may be a thermal bending transducer. The thermal bending transducer may be a bimetal strip having different coefficients of thermal expansion, for example. The thermal bending transducer 108 may also be a so-called bimorph. While the bimetal strip comprises two metals having different expansion coefficients, the bimorph generally has two different materials. For example, the bimorph may comprise a first active area comprising a metal and a second active area comprising silicon.

A thermal bending transducer may comprise, e.g., an active area which is thermally deformable. The thermal bending transducer is advantageously deflectable in a first direction as a function of the temperature. Following cooling, the thermal bending transducer returns to its original shape.

The thermal bending transducer may also comprise a shape memory alloy, or smart alloy.

The actuation means 108 may advantageously be configured to be deflected when a predefined threshold value is exceeded and/or fallen below, so as to move, by means of said deflection, the catch element 103 and the pawl 104 in relation to each other in the freewheeling direction 106 on a catch-by-catch basis.

In this respect, please refer to FIGS. 2 and 3A to 3F once again. The actuation means 108 here be thermally deflectable, for example. The actuation means 108, the catch element 103 and the pawl 104 are mutually arranged such that the catch element 103 jumps forward, in relation to the pawl 104, only by one tooth when a threshold-value temperature is exceeded. I.e., only when said threshold-value temperature is exceeded will the actuation means 108 be deflected to such an extent that it displaces the gearwheel 103 far enough for the pawl 104 to jump into the next tooth interstice. This means that the actuation means 108 is configured and dimensioned such that it will be deflected, when the threshold value is exceeded, to such an extent that it enables a catch-wise relative movement, i.e. a relative movement which continues precisely by one catch interstice, between the catch element 103 and the pawl 104.

However, if the threshold-value temperature is not reached, the actuation means 108 will not be deflected sufficiently so as to move the gearwheel 103 forward by one tooth.

For example, if a temperature cools down again once the threshold-value temperature has been exceeded, the thermally deflectable actuation means 108 will return to its initial position. Then the thermal actuation means 108 is again ready to be deflected again until the threshold-value temperature has been reached and to move the gearwheel 103 forward by one tooth, i.e. in a catch-wise manner.

Depending on the implementation of the actuation means 108, the above may take place not only when a threshold-value temperature is exceeded, but also when such a threshold-value temperature is fallen below.

Depending on the implementation of the actuation means 108, a force other than a thermal force may cause deflection of the actuation means 108, provided that the respective force falls below or exceeds a predefined threshold value.

Therefore, every time a threshold value is fallen below or exceeded, the catch element 103 may be moved forward, in relation to the pawl 104, by one catch 102a, 102b with the inventive device 100. Thus, a threshold-value counter may be implemented with the inventive device, said counter counting the number of times that the threshold value has been fallen below or exceeded.

An embodiment of such a threshold-value counter is proposed in the form of a counter of sterilization cycles, wherein the actuation means 108 displaces, upon each sterilization process, the catch element 103 and the pawl 104 relative to each other by one catch 102a, 102b, respectively, in the freewheeling direction.

An example of a temperature-related process is steam sterilization (autoclaving) when treating reusable instruments and components in a hospital environment. In a typical process sequence of steam sterilization, a maximum temperature level of 121° C. or 134° C. is reached once, depending on the process, as outlined in FIG. 10. Here, curve 1010 represents the temperature curve, and curve 1020 represents the pressure curve, over time.

Consequently, reaching and ascertaining the associated temperature threshold value may be seen as a characteristic of a successfully performed sterilization cycle. On the other hand, "enumerating" of the individual cycles enables detecting the overall number of sterilization cycles passed through, e.g. with regard to a maximum admissible number of steam sterilizations during the life cycle of an instrument.

For example, steam sterilization (heating inside an autoclave) is the standard procedure in most laboratories and hospitals in order to free materials and objects from living microorganisms, including their periods of dormancy (e.g. spores).

In this context, the articles to be sterilized, or the charge, are/is:
heated in water vapor at 121° C. at a pressure of 2 bar for 20 minutes, or
at 134° C. at 3 bar for 5 minutes, or
at 134° C. at 3 bar for 18 minutes (destruction of prions)

The inventive device exhibits user-specific advantages, i.e. it exhibits advantages for
a) equipment manufacturers:
number of sterilization cycles per piece of equipment, among other things because of warranty/utilization beyond the extent specified
question of warranty in particular with very high-quality pieces of equipment
b) equipment users:
verification as to whether and how often a piece of equipment has been sterilized/logistics Thus, some embodiments of the inventive device may be summarized as follows:
1. Thermally triggered actuator moves micromechanical structure (gearwheel) at critical temperature
2. Mechanical movement about "a catch" (=1 cycle) changes the capacitance
3. Change in capacitance changes characteristic of a passive RFID resonant circuit
4. Reading out the changed resonant circuit (=meter reading) with an active RFID reader Embodiments of the invention thus provide a MEMS sterilization-cycle counter which is self-sufficient in terms of energy and may be read out like a passive RFID tag.

The invention shall once again be described in different words below:

An embodiment of the invention provides a device, e.g. in the form of a microsystem (MEMS) which can autonomously, i.e. without any internal or external supply of electrical energy, count and store reaching of defined temperature threshold values and enables electrical readout of the number of temperature threshold-value events reached at a later point in time.

Thus, FIG. 2 schematically depicts, as an example of an inventive device, a MEMS temperature threshold-value counter which comprises the following components among others:
a substrate 210, e.g. a wafer made of silicon;
a toothed movable structure (catch element) 103 on the stationary substrate 210, e.g. on a freely rotating gearwheel, which was manufactured by means of silicon surface mechanics or bulk micromechanics;
a pawl 104 which enables movement of the tooth structure 103 in only one direction (freewheeling direction) 106, e.g. a blocking pawl which was also manufactured by means of silicon surface mechanics or bulk micromechanics;
a drive mechanism (actuation means) 108 which, with its thermally induced movement, moves the tooth structure 103 directly or with the aid of further elements, e.g. diversion, and moves it in a direction to opposite the direction blocked by the pawl 104, e.g. a thermal bending transducer made of two materials having different coefficients of temperature expansion;
an electric component 109 which interacts both with the substrate 210 and with the movable tooth structure 103 such that movement of the two parts 210, 103 relative to each other causes a unique change in the electrical properties of the component 109, e.g. when the stationary substrate 210 forms an electrode and when the movable tooth structure 103 forms the second electrode of a capacitor, so that displacement of the two electrodes relative to each other changes the capacitance of the electrical capacitor; and
an electronic interface 209, which need not necessarily be part of the MEMS element itself and enables readout of the change in the electric component 109, e.g. when the electric component 109 directly represents the adjustable member of an RFID resonant circuit or of more sophisticated electronics.

The exemplary mode of operation of the MEMS temperature threshold-value counter is once again depicted schematically in FIGS. 11A to 11D. When the critical temperature limit is exceeded and/or fallen below, the drive mechanism (actuation means) 108 performs a thermally induced movement, e.g. from the initial position (FIG. 11A) to the final position (FIG. 11C), in the course of which it moves the tooth structure (catch element) 103 and moves it by one step (tooth) 102a, 102b counter to the direction 107 blocked by the pawl 104. In the process, the tooth structure 103 glides past the pawl 104.

Figure 11A:
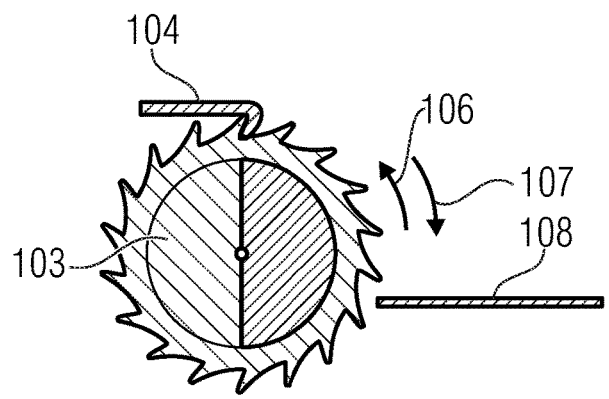
FIGS. 11A-11D show further detailed views for describing the mode of operation of the inventive device.
Figure 11B:
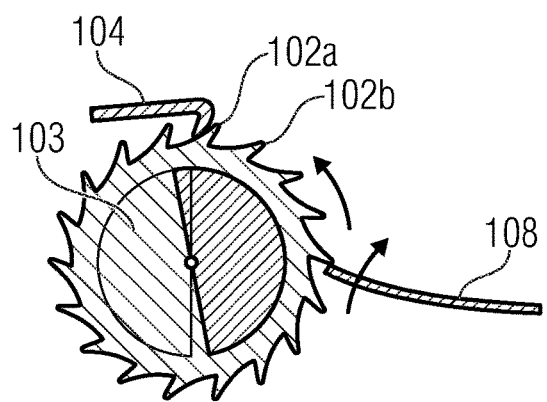
Figure 11C:
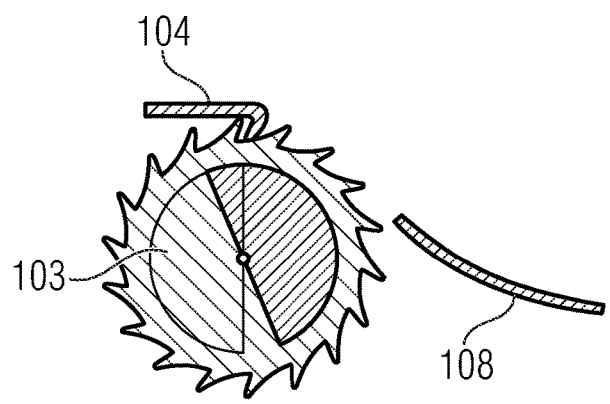
Figure 11D:
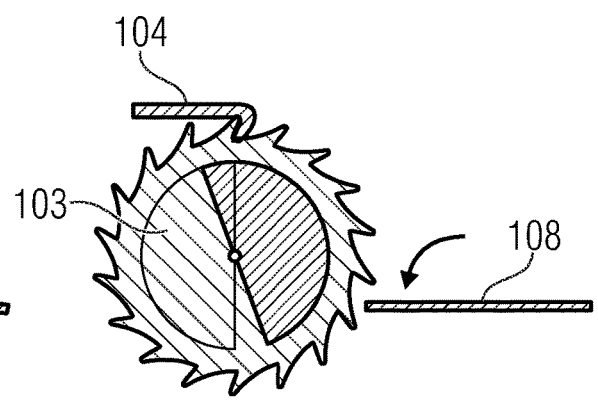

As long as the temperature limit is not fallen below or exceeded, the drive mechanism 108 will remain in the final position (FIG. 11C). However, if the temperature limit is fallen below and/or exceeded again, the mechanism will again perform a movement from the final position (FIG. 11C) to the initial position (FIG. 11D). In the course of this return movement, the drive mechanism 108 again comes into contact with the tooth structure 103. However, the pawl 104 prevents the tooth structure 103 from rotating back into the original position, so that the drive mechanism 108 may and can glide across the tooth structure 103.

Each time the temperature limit is exceeded or fallen below and is subsequently fallen below or exceeded, the described sequence repeats itself, wherein the tooth structure 103 is moved forward by one step (tooth) 102a, 102b in each case, and wherein the location of the tooth structure 103 in relation to the substrate 210 consequently changes.

Since with this movement, the property of the electric component 109 also uniquely changes, the property of the electric component 109 is characteristic of the location of the tooth structure 103 in relation to the substrate 210 and, thus, is characteristic of the number of steps performed up to then, or the number of teeth that have been jumped over up to then, which corresponds to the number of temperature threshold-value events that have taken place. The functions of the MEMS element which have been mentioned so far are performed in a manner that is self-sufficient in terms of energy, i.e. no supply of electrical energy is required.

With the aid of the electronic interface 209 explained with regard to FIG. 2, a user may at any time read out the properties of the electric component 109 and, thus, the temperature threshold-value events that have been taken place so far. To this end, there are various possibilities, three of which will be explained below by way of example.

1. In the simplest case, direct readout of the property of the electric component 109 is effected by means of wired contacting with a corresponding measuring device, which enables determining the temperature threshold-value events that have taken place.
2. If the electric component 109 corresponds to a typical element of a resonant circuit (capacitor, coil, resistor), e.g. a variable capacitor, and if same forms a resonant circuit 207 together with a coil structure 206, a change in capacitance will also result in a change in the resonant characteristic of the resonant circuit (depicted in FIG. 2). The resultant passive transponder an RFID system (radio-frequency identification) may be wirelessly read out by means of a corresponding reader, and, in turn, the temperature threshold-value events which have taken place may thus be determined.
3. If the electronic component 109 forms part of an electronic circuit, which in turn forms part of an RFID transponder system, electrical energy may be wirelessly coupled into the circuit by means of a corresponding reading device and may be used for performing functions of the electronic circuit, e.g. for signal amplification, signal evaluation and further transmission tasks.

As was already mentioned, the inventive concept may be used for determining different threshold-value events. One of several examples of this would be utilization as a sterilization-cycle counter. Here, for example, surgical instruments are sterilized by means of hot steam after utilization.

Generally, the inventive device exhibits the following advantages, among others:
  self-sufficient, in terms of energy, ascertainment of the temperature peak, no source of electrical energy required
  electrical readability of the meter by means of a passive RFID concept
  MEMS technology, consequently small component which may be widely used
  in large numbers expected to be lower in cost than FWT variant
  See transfer FWT rotation-rate sensor to a MEMS rotation-rate sensor
  counterfeit-proof since it can be excluded that fewer cycles than registered have taken place
  Possible technical features:
  bending actuator at the wafer level
  freely rotating microstructure with latching mechanisms
  combination of a mechanically adjustable capacitor with a passive RFID resonant circuit
  Further ideas of implementation:
  adjust a coil instead of a capacitor: coil spring, two coil springs interleaved with each other
  Of course, the above-mentioned examples are not exhaustive or limiting. Further embodiments may be provided which may be categorized as follows:
  By means of the setup of the tooth structure:
  a) Tooth structure
    a. freely rotating (FIG. 2)
    b. deflectable via a flexure bearing/spring
    c. stationary
  b) Movable tooth structure
    a. radial inner and/or outer toothing (FIG. 2)
    b. linear inner and/or outer toothing (rack rail)
  By means of the operational sequence:
  a) tooth structure passive+catch passive→drive moves gearwheel (FIGS. 2, 3A to 3F)
  b) tooth structure biased→drive moves latching mechanism (principle of anchor escapement—FIG. 6), i.e. catch and drive form one unit
  c) tooth structure stationary, drive with catch "pulls" itself across the tooth structure
  By means of a change in the electric component:
  a) capacitor
  b) coil
  c) resistor (ohmic and/or piezoresistive)
  d) electro-optical element
  In addition, embodiments of the actuation means 108 will be proposed below:
  thermal bending transducers (bimorph actuators) which may be constructed from two materials having different coefficients of thermal expansion and which may move, in particular, in parallel to or within the wafer level, the latter being technologically of high interest in the present case
  shape memory alloys
  actuators which directly exploit thermal solid-body expansion and are then possibly transmitted for increasing the stroke (e.g. by means of angular structures, "Chevron structures")

exploiting the change in volume of a liquid exploiting the change in volume in a thermal phase change In addition to the temperature, which was already mentioned, it is also possible with the inventive device 100 to take into account acceleration, pressure, etc. as a possible threshold-value event, which is why the inventive device may also be referred to as a threshold-value indicator and/or a threshold-value determiner. A property which the inventive device 100 exhibits is the possibility to ensure, with the approach described herein, that jumping forward involves only one catch, or one tooth, for each threshold-value event.

Further feasible embodiments of an inventive device therefore may be the following, for example:

Autonomous MEMS threshold-value counter (e.g. temperature threshold-value counter) comprising:

a substrate 210 (substrate includes—when one thinks of a closed housing—both a "bottom" and a "cover" as well as "sides")

a movable structure 103 provided with teeth 102*a*, 102*b* a thermally operated drive mechanism 108 a readable electric component 109 interacting both with the movable structure 103 and with the substrate 210, wherein, when a temperature threshold value is exceeded or fallen below, the drive mechanism 108 moves the structure provided with teeth 102*a*, 102*b*, and wherein the electrical properties of the electric component 109 change as a result.

Further feasible embodiments will be listed below in bullet point form:

the temperature threshold-value counter may be manufactured in silicon technology a mechanism may prevent the return movement of the movable structure 103 upon the return movement of the drive mechanism 108 the structure 103 provided with teeth 102*a*, 102*b* may not comprise a fixed connection with the substrate 210 the movable structure 103 provided with teeth 102*a*, 102*b* may be a freely rotating gearwheel the structure 103 provided with teeth 102*a*, 102*b* may be a linearly displaceable element the structure 103 provided with teeth 102*a*, 102*b* may be connected to the substrate 210 via a flexure bearing the electric component 109 may be an adjustable member of an RFID resonant circuit 207 it may be a passive RFID resonant circuit 207 the electric component 109 may be a capacitor a resistor a coil the electric component 109 may be connected to electronics the electronics in turn may be part of an RFID resonant circuit 207 the electronics may reinforce the change in the electric component 109 the electronics may be supplied with energy via the RFID resonant circuit 207 the drive mechanism 108 may be a bending transducer it may be a thermal bimorph actuator the expansion may be a thermal solid-body expansion the drive mechanism 108 may act upon the element 103 provided with teeth 102*a*, 102*b* by means of low- and high-speed transmission the low- and/or high-speed transmission may convert a movement that is parallel to the substrate surface to a movement that takes place within the substrate plane the temperature threshold-value counter may detect a defined temperature threshold value being exceeded the temperature threshold-value counter may be employed as a sterilization-cycle counter The present invention may further be implemented in the form of the following embodiments:

A first embodiment relates to a device (100) comprising a latching mechanism (101) comprising a catch element (103) having at least two catches (102*a*, 102*b*), and a pawl (104) configured to engage in a catch interstice (105) between two catches (102*a*, 102*b*), wherein the catch element (103) is movable in relation to the pawl (104) in a freewheeling direction (106), and a movement of the catch element (103) in relation to the pawl (104) in a blocking direction (107) may be blocked by means of the pawl (104), deflectable actuation means (108) configured to move the catch element (103) and the pawl (104) relative to each other on a catch-by-catch basis in the freewheeling direction (106) by means of a deflection, and an electric component (109) configured to change its electric property as a function of the catch-wise movement of the catch element (103) in relation to the pawl (104).

In accordance with a second embodiment while referring to the first embodiment, the latching mechanism (101) may be configured as a microsystem (MEMS: micro-electromechanical system).

In accordance with a third embodiment while referring to the first or second embodiment, the device (100) may further comprise a substrate (210) which has the latching mechanism (101) provided thereon as a MEMS, wherein deflection of the actuation means (108) takes place within a plane that is horizontal to the substrate plane.

In accordance with a fourth embodiment while referring to the first or second embodiment, the device (100) may further comprise a substrate (210) which has the latching mechanism (101) provided thereon as a MEMS, wherein deflection of the actuation means (108) takes place within a plane that is perpendicular to the substrate plane, and the device (100) further comprising a diverting device (700) by means of which the deflection movement of the actuation means (108), which is directed perpendicularly to the substrate plane, may be diverted to a movement that is directed horizontally to the substrate plane.

In accordance with a fifth embodiment while referring to any of the previous embodiments, the catches (102*a*, 102*b*) may be arranged one behind the other along the catch element (103) in the freewheeling direction (106), so that the pawl (104) will consecutively engage, in the catch-wise movement, from one catch interstice (105*a*) into the respectively next adjacent catch interstice (105*b*).

In accordance with a sixth embodiment while referring to any of the previous embodiments, the catch element (103) may be a freely rotatable gearwheel wherein the catches (102*a*, 102*b*) are configured in the form of a toothing arranged radially on the outside or on the inside of the gearwheel (103).

In accordance with a seventh embodiment while referring to any of the previous embodiments, the catch element (103) may be a rack that is movable in relation to the pawl (104) and wherein the catches (102*a*, 102*b*) are configured in the form of a toothing arranged on the rack (103).

In accordance with an eighth embodiment while referring to any of the previous embodiments, the actuation means (108) may actuate the catch element (103) to move the catch element (103) further by one catch (102a, 102b), respectively, on a catch-by-catch basis in relation to the pawl (104) in the freewheeling direction (106).

In accordance with a ninth embodiment while referring to the eighth embodiment, the actuation means (108) may act upon a catch (102a, 102b) of the catch element (103) so as to move the catch element (103) further, on a catch-by-catch basis, in relation to the pawl (104).

In accordance with a tenth embodiment while referring to any of the previous embodiments, the catch element (103) may be biased by means of a tensioning element (501), and the actuation means (108) may actuate the pawl (104), wherein upon a movement of the pawl (104), which releases the engagement with a catch interstice (105a), the biased catch element (103) is moved forward by one catch (102a, 102b) in each case due to the bias before the pawl (104) engages in an adjacent next catch interstice (105b) of the catch element (103) again.

In accordance with an eleventh embodiment while referring to any of the previous embodiments, the actuation means (108) may be thermally deflectable.

In accordance with a twelfth embodiment while referring to any of the previous embodiments, the actuation means (108) may be a thermal bending transducer and/or the actuation means (108) may comprise a shape memory alloy.

In accordance with a thirteenth embodiment while referring to any of the previous embodiments, the actuation means (108) may be mechanically or electrically deflectable.

In accordance with a fourteenth embodiment while referring to any of the previous embodiments, the actuation means (108) may be configured to be deflected once a predefined threshold value is exceeded or fallen below so as to move, by means of said deflection, the catch element (103) and the pawl (104) in relation to each other on a catch-by-catch basis in the freewheeling direction (106).

In accordance with a fifteenth embodiment while referring to any of the previous embodiments, the electric component (109) may be a capacitor or a resistor or a coil or an electro-optical element.

In accordance with a sixteenth embodiment while referring to any of the previous embodiments, the electric component (109) may be an adjustable member of an RFID resonant circuit (207).

In accordance with a seventeenth embodiment while referring to any of the previous embodiments, the device (100) may further comprise a substrate (210) which has the latching mechanism (101) arranged thereon, and the electric component (109) may be arranged between the latching mechanism (101) and the substrate (210).

In accordance with an eighteenth embodiment while referring to any of the previous embodiments, the device (100) may further comprise a substrate (210) on which the latching mechanism (101) is provided, and the electric component (109) may be a capacitor, wherein a first capacitor plate (201) is provided at the substrate (210) and a second capacitor plate (202) is provided at the catch element (103) and/or at the pawl (104), and wherein upon catch-wise movement of the catch element (103) and/or of the pawl (104) in relation to the substrate (210), mutual alignment of the capacitor plates (201, 202) changes, the capacitance of the capacitor changing.

In accordance with a nineteenth embodiment while referring to any of the previous embodiments, the device (100) may be configured as a sterilization-cycle counter, wherein the actuation means (108) shifts, with each sterilization process, the catch element (103) and the pawl (104) by one catch (102a, 102b), respectively, in relation to each other in the freewheeling direction (106).

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

SOURCES

[1] X.-Q. Sun, S. Zhou, and W. N. Carr "A surface micromachined latching accelerometer", International Conference on Solid State Sensors and Actuators 1997, 1189-1192.

[2] H. Mehner, C. Weise, S. Schwebke, S. Hampl, M. Hoffmann, "A passive microsystem for detecting multiple acceleration events beyond a threshold", Microelectronic Engineering 145 (2015), 104-111

The invention claimed is:

1. Device comprising
a latching mechanism arranged on a substrate and comprising a catch element comprising at least two catches, and a pawl configured to engage in a catch interstice between two catches,
wherein the catch element is movable in relation to the pawl in a freewheeling direction and wherein a movement of the catch element in relation to the pawl in a blocking direction may be blocked by means of the pawl,
a deflectable actuator configured to move the catch element and the pawl relative to each other on a catch-by-catch basis in the freewheeling direction by means of a deflection, and
an electric component configured to change its electric property as a function of the catch-wise movement of the catch element in relation to the pawl,
wherein the latching mechanism is configured as a MEMS microsystem.

2. Device as claimed in claim 1, wherein the electric component is a capacitor, wherein a first capacitor plate is provided at the substrate and a second capacitor plate is provided at the catch element and/or at the pawl, and wherein upon catch-wise movement of the catch element and/or of the pawl in relation to the substrate, the mutual alignment of the capacitor plates in relation to each other changes, wherein the capacitance of the capacitor changes.

3. Device as claimed in claim 1, wherein deflection of the actuator takes place within a plane that is horizontal to the substrate plane.

4. Device as claimed in claim 1, wherein deflection of the actuator takes place within a plane that is perpendicular to the substrate plane, and the device further comprising a diverting device by means of which the deflection movement of the actuator, which is directed perpendicularly to the substrate plane, may be diverted to a movement that is directed horizontally to the substrate plane.

5. Device as claimed in claim 1, wherein the catches are arranged one behind the other along the catch element in the freewheeling direction, so that the pawl will consecutively engage, in the catch-wise movement, from one catch interstice into the respectively next adjacent catch interstice.

6. Device as claimed in claim 1, wherein the catch element is a freely rotatable gearwheel wherein the catches are configured in the form of a toothing arranged radially on the outside or on the inside of the gearwheel.

7. Device as claimed in claim 1, wherein the catch element is a rack that is movable in relation to the pawl and wherein the catches are configured in the form of a toothing arranged on the rack.

8. Device as claimed in claim 1, wherein the actuator actuates the catch element to move the catch element further by one catch, respectively, on a catch-by-catch basis in relation to the pawl in the freewheeling direction.

9. Device as claimed in claim 8, wherein the actuator acts upon a catch of the catch element so as to move the catch element further, on a catch-by-catch basis, in relation to the pawl.

10. Device as claimed in claim 1, wherein the catch element is biased by means of a tensioning element and wherein the actuator actuates the pawl, wherein upon a movement of the pawl, which releases the engagement with a catch interstice, the biased catch element is moved forward by one catch in each case due to the bias before the pawl engages in an adjacent next catch interstice of the catch element again.

11. Device as claimed in claim 1, wherein the actuator is thermally deflectable.

12. Device as claimed in claim 11, wherein the actuator is a thermal bending transducer, or wherein the actuator comprises a shape memory alloy.

13. Device as claimed in claim 1, wherein the actuator is mechanically or electrically deflectable.

14. Device as claimed in claim 1, wherein the actuator is configured to be deflected once a predefined threshold value is exceeded or fallen below so as to move, by means of said deflection, the catch element and the pawl in relation to each other on a catch-by-catch basis in the freewheeling direction.

15. Device as claimed in claim 1, wherein the electric component is a resistor or a coil or an electro-optical element.

16. Device as claimed in claim 1, the device comprising an RFID resonant circuit, wherein the electric component is an adjustable member of the RFID resonant circuit.

17. Device as claimed in claim 1, wherein the electric component is arranged between the latching mechanism and the substrate.

18. Device as claimed in claim 1, the device being configured as a counter of sterilization cycles, wherein the actuator shifts, with each sterilization process, the catch element and the pawl by one catch, respectively, in relation to each other in the freewheeling direction.

* * * * *